(12) United States Patent
Zvuloni et al.

(10) Patent No.: US 6,875,209 B2
(45) Date of Patent: Apr. 5, 2005

(54) CRYOPLASTY APPARATUS AND METHOD

(75) Inventors: Roni Zvuloni, Haifa (IL); Mordechai Bliweis, Haifa (IL); Doris Schechter, Yakov (IL); Uri Amir, Yehuda (IL); James McGlone, Garden City, NY (US)

(73) Assignee: Galil Medical Ltd., Yokneam (IL)

( * ) Notice: Subject to any disclaimer, the term of this patent is extended or adjusted under 35 U.S.C. 154(b) by 104 days.

(21) Appl. No.: 10/255,834

(22) Filed: Sep. 27, 2002

(65) Prior Publication Data

US 2003/0060762 A1 Mar. 27, 2003

Related U.S. Application Data

(60) Provisional application No. 60/324,937, filed on Sep. 27, 2001, and provisional application No. 60/357,653, filed on Feb. 20, 2002.

(51) Int. Cl.[7] ............................................. A61B 18/18
(52) U.S. Cl. ...................................................... 606/21
(58) Field of Search ...................................... 606/20–26

(56) References Cited

U.S. PATENT DOCUMENTS

| 5,147,355 | A | | 9/1992 | Friedman et al. | |
|---|---|---|---|---|---|
| 5,431,648 | A | * | 7/1995 | Lev | 606/27 |
| 5,868,735 | A | | 2/1999 | Lafontaine | |
| 5,971,979 | A | | 10/1999 | Joye et al. | |
| 6,290,696 | B1 | | 9/2001 | Lafontaine | |
| 6,355,029 | B1 | | 3/2002 | Joye et al. | |
| 6,517,533 | B1 | * | 2/2003 | Swaminathan | 606/20 |
| 6,575,966 | B2 | * | 6/2003 | Lane et al. | 606/21 |
| 6,602,246 | B1 | * | 8/2003 | Joye et al. | 606/21 |
| 6,652,565 | B1 | * | 11/2003 | Shimada et al. | 607/105 |
| 2002/0010460 | A1 | | 1/2002 | Joye et al. | |
| 2002/0032438 | A1 | | 3/2002 | Lafontaine | |
| 2002/0045892 | A1 | | 4/2002 | Kramer | |
| 2002/0045894 | A1 | | 4/2002 | Joye et al. | |

* cited by examiner

Primary Examiner—Michael Peffley
(74) Attorney, Agent, or Firm—G.E. Ehrlich (1995) Ltd.

(57) ABSTRACT

The present invention relates to apparatus, systems, and methods utilizing cryogenic cooling in an angioplasty balloon catheter for treatment of arterial stenosis and prevention of restenosis. More particularly, the present invention relates to an angioplasty balloon catheter utilizing expansion of compressed gas to effect Joule-Thomson cooling of an angioplasty balloon, and optionally further incorporating external temperature sensors utilizable to identify a locus for treatment of arterial stenosis. The present invention further relates to angioplasty treatment systems incorporating such a catheter, and to cryogenic angioplasty methods for treating arterial stenosis and discouraging restenosis.

6 Claims, 19 Drawing Sheets

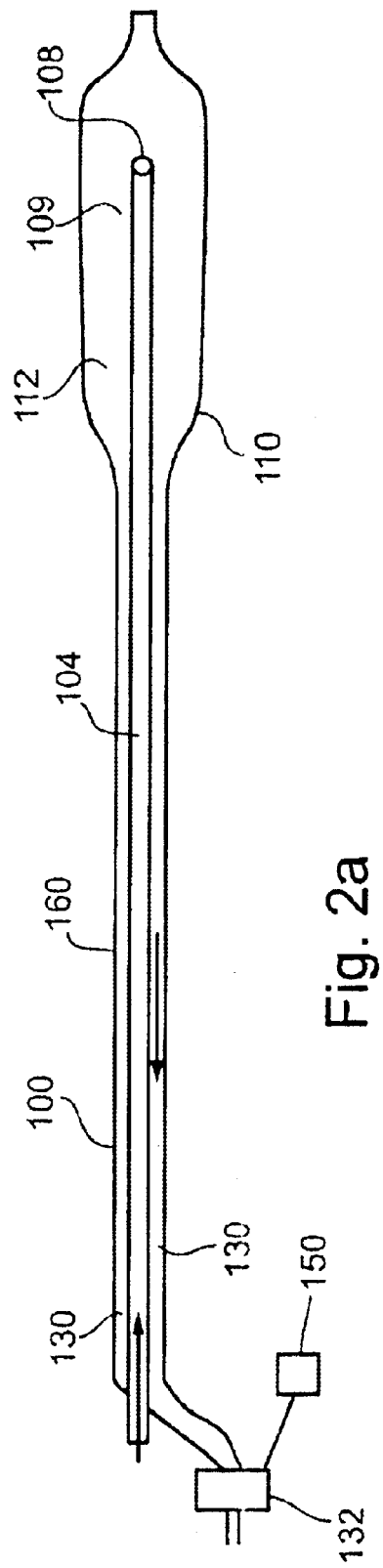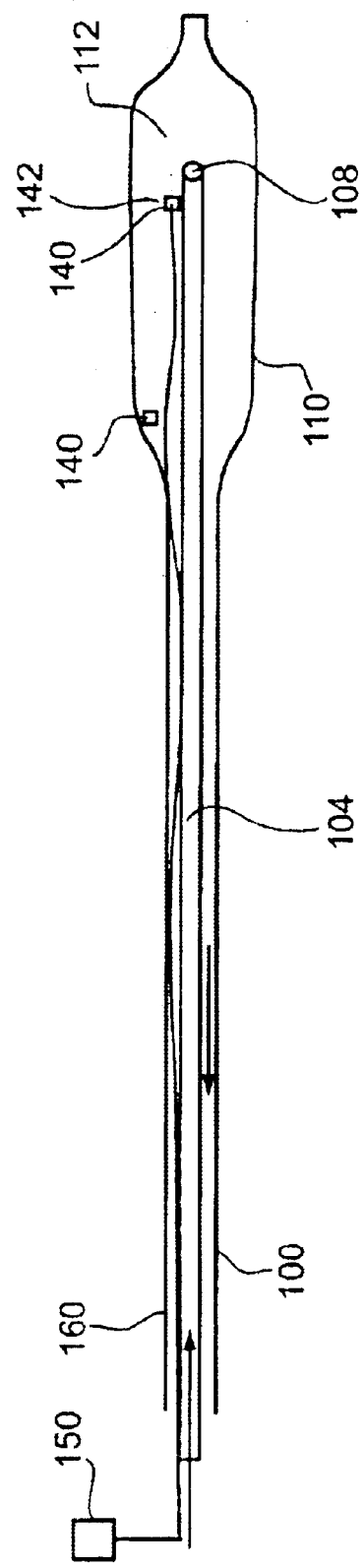
Fig. 2a
Fig. 2b

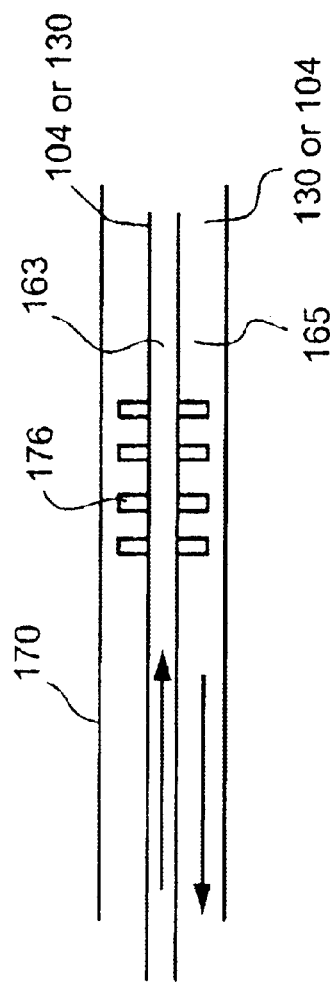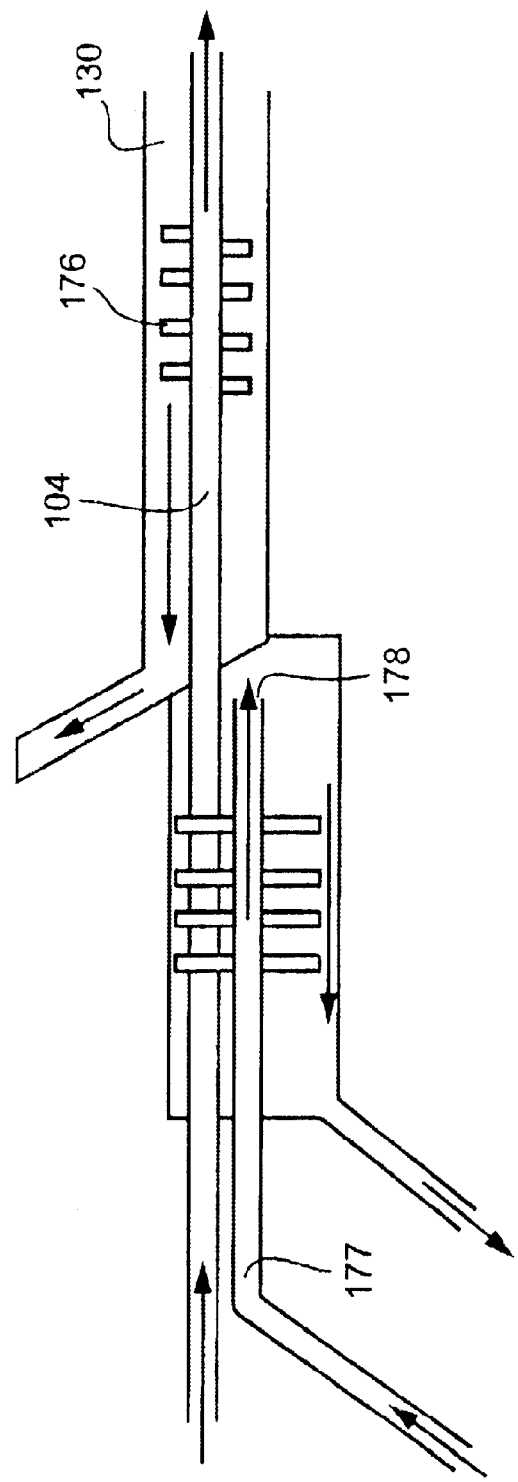

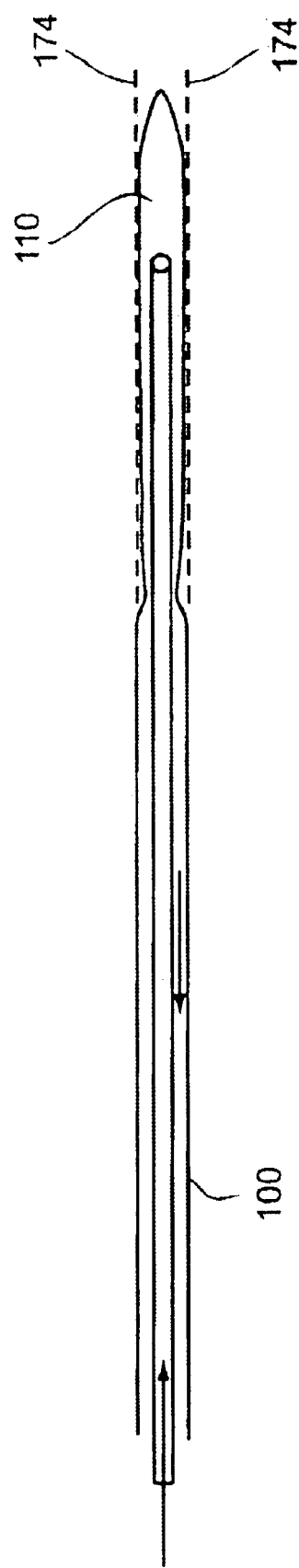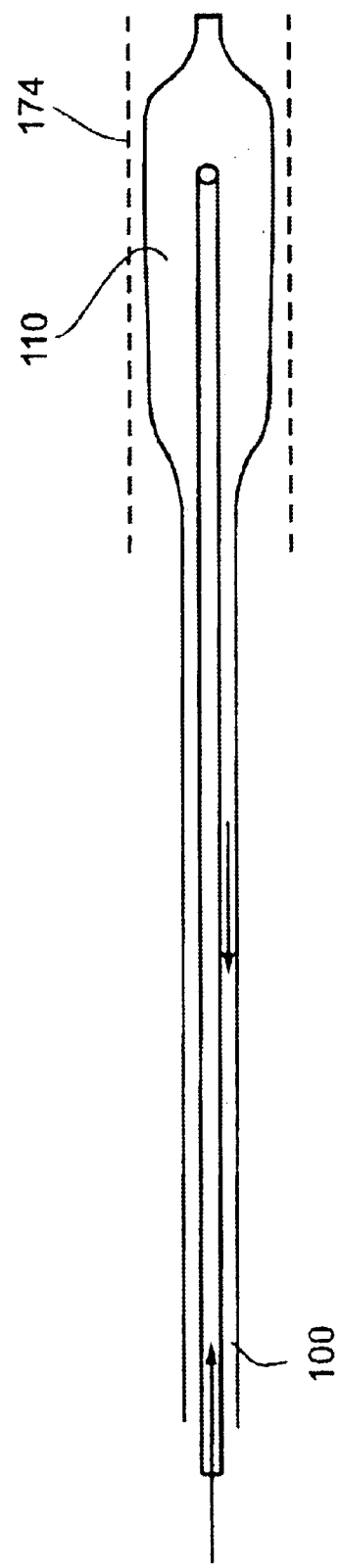
Fig. 4a
Fig. 4b

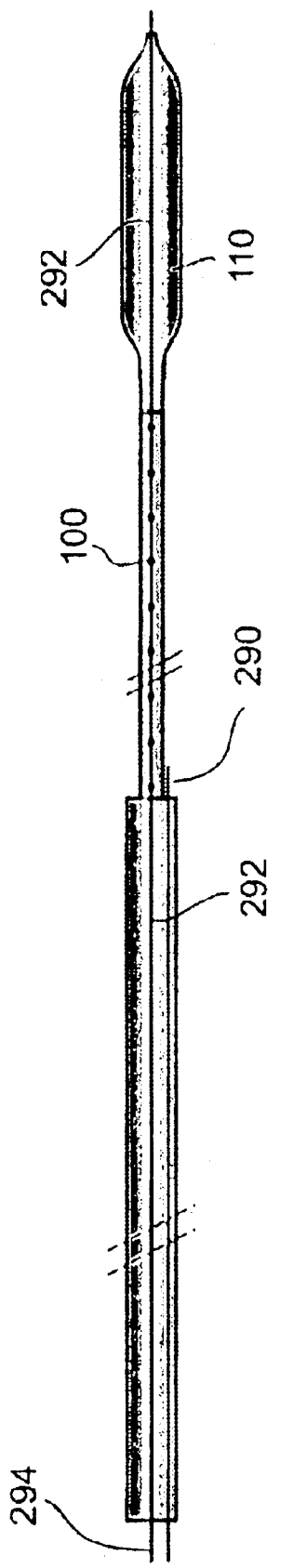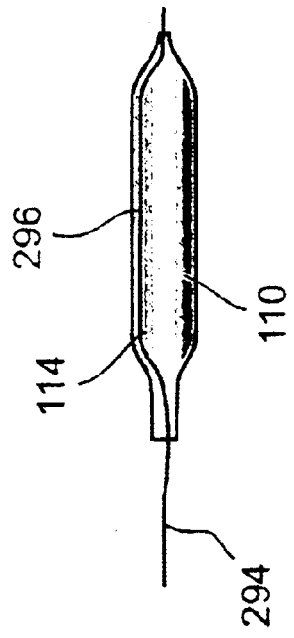
Fig. 13
Fig. 14

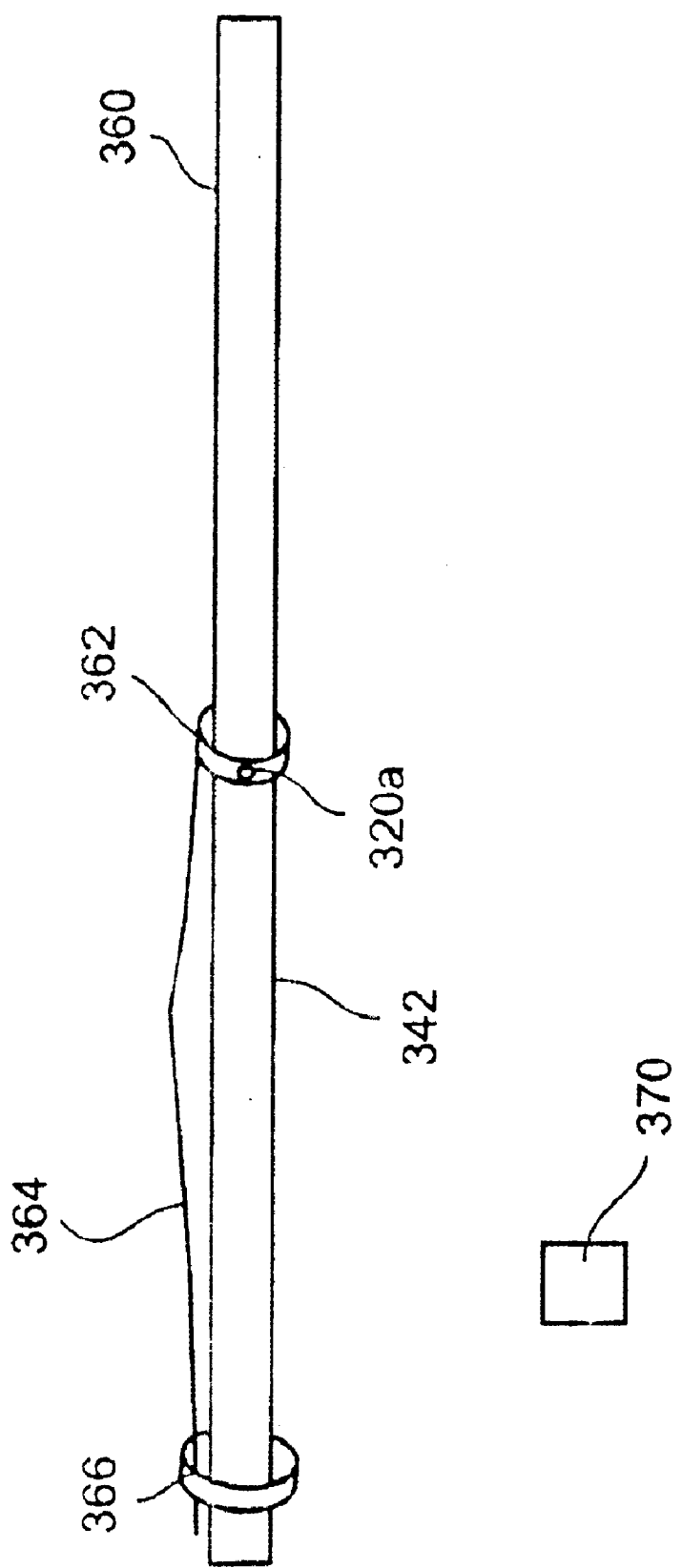

CRYOPLASTY APPARATUS AND METHOD

This application claims the benefit of priority from U.S. Provisional Patent Application No. 60/324,937, filed Sep. 27, 2001, and U.S. Provisional Patent Application No. 60/357,653, filed Feb. 20, 2002, the contents thereof are incorporated herein by reference.

FIELD AND BACKGROUND OF THE INVENTION

The present invention relates to apparatus, systems, and methods utilizing cryogenic cooling in an angioplasty balloon catheter for treatment of arterial stenosis and prevention of restenosis. More particularly, the present invention relates to an angioplasty balloon catheter utilizing expansion of compressed gas to effect Joule-Thomson cooling of an angioplasty balloon, and optionally further incorporating external temperature sensors utilizable to identify a locus for treatment of arterial stenosis. The present invention further relates to angioplasty treatment systems incorporating such a catheter, and to cryogenic angioplasty methods for treating arterial stenosis and discouraging restenosis.

It is a well-known problem of angioplastic surgery that blood vessels having been subjected to angioplastic treatment have a marked tendency to undergo restenosis. Blood vessels having displayed improved vascular flow as result of an angioplasty intervention are often observed to suffer a subsequent re-narrowing of the vessel, again impeding vascular flow, in the weeks and months following the angioplasty intervention. Such restenosis is currently understood to be a reaction of vascular tissues to the angioplastic procedure, or to the ongoing endovascular insult.

Cooling of the site during or immediately following angioplasty has been found to impede or prevent restenosis. A number of patents have been issued relating to devices for cryogenic cooling of tissues during or after angioplasty, and to angioplasty methods using cooling devices.

U.S. Pat. No. 5,868,735 to Daniel M. Lafontaine, and U.S. Pat. No. 4,290,686 also to Lafontaine, both refer to cryogenic cooling of an angioplasty apparatus, as does U.S. Patent Application 20020032438 by Lafontaine.

Lafontaine teaches a method whereby a balloon catheter is advanced to a target site, the balloon is inflated, and coolant is delivered into the inflated balloon to freeze a portion of a lesion adjacent to the balloon, to kill cells within the lesion.

It is, however, a limitation of the above-mentioned Lafontaine patents and patent application that the implementations described are limited to cryogenic cooling by evaporation of a liquid.

As is well known, evaporation from a liquid cools that liquid. If a liquid, such as for example liquid nitrogen, is maintained under pressure to prevent boiling, and then is passed into an area where it is free to expand, released pressure allows boiling or rapid evaporation of the liquid, cooling both the liquid and the resultant gas.

Cooling by evaporation is described by Lafontaine as the method of choice for cryogenic cooling of a cryoplasty balloon catheter to effect cooling of tissues at an angioplasty site. We note that although claim 13 of U.S. Pat. No. 6,290,696 op. cit. is couched in general terms, in that Lafontaine refers to delivering coolant into the balloon and allowing the coolant to undergo a phase change within the balloon, the phase change actually described within Lafontaine's disclosure is a phase change from liquid to gas, that is, cooling by evaporation.

U.S. patent application Ser. No. 20020010460, submitted by James Joye et. al. similarly refers to a cryosurgery probe usable to perform angioplasty, which probe enables cryogenic cooling of tissues at an angioplasty site. Joye refers to an apparatus in which a single balloon may function for both cryogenic cooling and for dilation.

Joye's application similarly contemplates cooling by evaporation. Throughout his disclosure, Joye presents and discusses cooling by evaporation from supplied cooling liquids or liquid/gas mixtures such as carbon dioxide ($CO_2$), nitrous oxide ($N_2O$), liquid nitrogen ($N_2$), a fluorocarbon such as AZ-50.TM. (sold by Genetron of Morristown, N.J.), or the like. Similar systems are presented U.S. Pat. No. 6,355,029 to Joye et. al. and in U.S. Pat. No. 5,971,979, also to Joye et. al.

It is to be noted that in each of the above-mentioned documents Joye refers in passing to the possibility of use of a Joule-Thomson orifice in the delivery of a cryogenic cooling fluid into an angioplasty balloon, yet in each of the documents, all of the implementation details refer to delivery of a liquid rather than a gas into a balloon or other volume to be cryogenically cooled. In this sense, the embodiments described in detail by Joye are similar to those described by Lafontaine in the patents cited hereinabove, in that evaporation of a liquid, a phase transition from a liquid to a gaseous state, is the cooling mechanism described. Thus, for example, Joye states in one context "the cryogenic fluid will flow through the tube 22 as a liquid at an elevated pressure and (thus inhibiting flow restrictive film boiling) will expand across the orifice 23 to a gaseous state at a lower pressure within the balloon." And similarly: "The methods of the present invention may be performed with cryosurgical catheters comprising a catheter body having a proximal end, a distal end, and a primary lumen therethrough. The primary lumen terminates in a Joule-Thomson orifice at or near its distal end, and a balloon is disposed over the orifice on the catheter body to contain a cryogenic fluid delivered through the primary lumen. Suitable cryogenic fluids will be non-toxic and include liquid nitrogen, liquid nitrous oxide, liquid carbon dioxide, and the like. By delivering the cryogenic fluid through the catheter body, the balloon can be expanded and cooled in order to effect treatments according to the present invention."

Thus, it is to be noted that although Joye employs the term "Joule-Thomson orifice", he uses it to describe a system wherein a pressurized liquid passes into a region where it is enabled to evaporate, thereby to effect cooling. This is to be contrasted to the embodiments to be described hereinbelow, wherein the cryogenic fluid delivered to an expandable balloon is a pressurized gas, not a liquid nor a liquid/gas mixture, and wherein expansion of a pressurized gas, and not evaporation of a liquid, is the cooling mechanism. Although the two methods are similar in that both allow for expansion of a compressed fluid, they are also, in a sense, almost opposite, in that the phase change initiated by delivery of a pressurized liquid into the balloon volume is a phase change from liquid to gas, whereas in a true Joule-Thomson delivery system a gas is allowed to expand, and by expansion to cool, and the result of that cooling process may even be, in some cases, a phase transition in the opposite direction, whereby the expanded gas is cooled to such an extent that a portion of the expanded gas actually condenses back into liquid phase.

Various other patents similarly refer to cooling by evaporation as a method of cryogenic cooling of an angioplasty balloon catheter. U.S. patent application Ser. No. 20020045892 by Hans W. Kramer is an additional example of a system utilizing evaporation of a liquid such as perfluorocarbon to achieve cryogenic cooling in a balloon catheter. U.S. Pat. No. 5,147,355 to Peter Friedman is yet another example of a system utilizing evaporation of a liquid to achieve cryogenic cooling.

Cooling by evaporation, however, presents a variety of disadvantages.

Cooling by evaporation is relatively slow when compared, for example, to true Joule-Thomson cooling, that is, when cooling by evaporation is compared to cooling by allowing rapid expansion of a compressed gas.

Further, evaporative cooling is not amenable to exact control of the cooling process, because evaporation is not instantaneous. Introducing into an angioplasty balloon a liquid which cools by evaporation inevitably introduces an intrinsic lag in any possible control of the cooling process, because halting the supply of cooling fluid does not immediately halt cooling. Liquid previously introduced into a balloon and not yet evaporated will continue to cool even after supply of additional cooling liquid has been halted. In the surgical context of angioplasty interventions, where treatment typically necessitates blocking of arteries during a procedure, speed of operation and fine control of temperatures are of great importance.

Thus, there is a widely felt need for, and it would be highly advantageous to have, an apparatus and method of cooling an angioplasty balloon which provide for rapid cooling and optional rapid heating of an angioplasty balloon, and which enable accurate, rapid, and exact control of temperatures within the angioplasty balloon and/or in the treated body tissues.

Joye's discussion of uses of his invention, in the documents cited above, points up several additional problematic aspects of cryogenic cooling by evaporation. Joye describes the difficulty of achieving an optimal cooling temperature at a target region, and further describes the difficulty of achieving an even cooling distribution throughout a target region.

With respect to maintenance of a desired temperature within the cooling apparatus, Joye points out that it is in many cases desirable to invoke apoptosis and/or programmed cell death so as to inhibit hyperplasia and/or neoplasia of a blood vessel related to angioplasty, stenting, rotational or directional artherectomy, or the like, and he further points out that in order to invole apoptosis (rather than simply destroying tissues by radical deep freezing) it will often be desirable to provide more moderate cryogenic treatment temperatures than those automatically provided by an uncontrolled evaporation process. Joye does not, however, provide a method of achieving exact control of cooling within the target regions. Indeed, he points out that cooling is generally enhanced by minimizing pressure within the angioplasty balloon. This link, between pressure of gas within an inflated balloon and the amount of cooling of that balloon, is one of the disadvantages of using an evaporation process to achieve cryogenic cooling of an angioplasty balloon.

Thus, there is a widely recognized need for, and it would be highly advantageous to have, an apparatus and method of cryogenic cooling in an angioplasty balloon catheter which provides for exact control of temperature within a balloon in a manner relatively independent of the dilation pressure maintained in that balloon.

With respect to the well-known difficulty of achieving an even cooling distribution throughout a target region, Joye discusses the fact that evaporative cooling tends to cool an apparatus unevenly, parts of the apparatus adjacent to a lumen through which cooling fluid is supplied being significantly colder than more distant parts of the apparatus. In an attempt to deal with the problem, Joye proposes a method distribution of a cryogenic liquid from a supply lumen into a cryogenic balloon, utilizing a diffuser that causes the cooling fluid to be distributed both radially and axially. The contemplated diffuser comprises a tubular structure with radially oriented openings. Joye points out that as the openings are radially oriented, the diffuser will direct the cooling fluid roughly perpendicularly toward the wall of the cryogenic balloon, thereby encouraging even heat transfer between the cooling vapor and balloon wall. Joye teaches that distribution of ports circumferentially and axially along the balloon provides a substantially uniform cooling over a significant portion of (often over the majority of) the surface of the balloon. A similar system is also described by Joye in U.S. Pat. No. 6,355,029. We note however that according to Joye's own description, the desired uniformity is not expected to extend over the entire surface of the balloon, and in many cases will not extend even to the majority of the balloon surface.

Thus, there is a widely recognized need for, and it would be highly advantageous to have, apparatus and method of cryogenic cooling of the balloon of an angioplasty balloon catheter, which method and apparatus provide for accurate control of temperature of the balloon during cooling, and further provide a highly evenly distribution of cold throughout that balloon catheter.

With respect to another aspect of cryogenic balloon angioplasty, U.S. patent application Ser. No. 20020045894 by James Joye et. al. presents an additional system for cryogenic cooling by evaporation, this system comprising a double balloon catheter, a first balloon being inflated by a pressurized gas, and a second balloon containing the first balloon, with a vacuum between the two. In U.S. patent application Ser. No. 20020045894 Joye presents a safety interlock system, whereby a rise in pressure in the outer balloon is interpreted to signal a leak in the inner balloon, and detection of such a rise in pressure causes his system to cut off supply of pressurized fluid to the inner balloon, thereby avoiding an irruption of pressurized fluid into the tissues of a patient undergoing a surgical intervention. We note, however, a disadvantage of the described safety interlock system, in that it is designed to detect such a leak only after a significant rise in pressure has occurred within the outer balloon.

Thus, there is a widely recognized need for, and it would be highly advantageous to have, a system for detecting a leak in such a balloon angioplasty system, which detection is highly sensitive to even very small leaks in an inner angioplasty balloon, thereby enabling to immediately cease supply of input fluids, and to undertake other or additional corrective measures, as soon as such a very small leak is detected, and without necessitating waiting for a leak large enough to significantly raise pressure in an outer balloon volume.

Referring now to other aspects of prior art, it is noted that one of the basic problems inherent in angioplasty and similar surgical interventions is the need to effect correct placement of an angioplasty balloon catheter prior to performance of angioplasty. There is thus a widely recognized need for, and it would be highly advantageous to have, apparatus and method enabling accurate placement of an angioplasty balloon catheter based information garnered at a potential intervention site, by an angioplasty balloon catheter, in real time.

SUMMARY OF THE INVENTION

According to one aspect of the present invention there is provided an angioplasty balloon catheter useable to treat arterial stenosis, comprising a gas input lumen for supplying a pressurized gas, a first inflatable balloon containing a first variable volume, and a Joule-Thomson orifice for passing the pressurized gas from the gas input lumen into the first variable volume so as to cool and inflate the first inflatable balloon.

According to further features in preferred embodiments of the invention described below, the catheter further comprises a first gas exhaust lumen for exhausting gas from the first variable volume of the first inflatable balloon. The catheter may comprise an exhaust control valve for controlling exit of exhaust gasses from the first gas exhaust lumen, and the exhaust control valve may be operable to regulate pressure within the first variable volume.

According to still further features in preferred embodiments of the invention described below, the catheter further comprises a heat exchanging configuration designed and constructed to facilitate transference of heat energy between the gas input lumen and the first gas exhaust lumen. The first gas exhaust lumen may be positioned contiguous to at least a portion of the gas input lumen, thereby constituting a heat exchanging configuration. The heat exchanging configuration may comprise a section wherein the gas input lumen is positioned within the first gas exhaust lumen and may have fins for facilitating heat exchange. Alternatively, first gas exhaust lumen may be positioned within the gas input lumen, and may have fins for facilitating heat exchange. Alternatively, the heat exchanging configuration comprises a section wherein the gas input lumen is spirally wrapped around the first gas exhaust lumen. Alternatively, the heat exchanging configuration comprises a section wherein the first gas exhaust lumen is spirally wrapped around the gas input lumen. The heat exchanging configuration may comprise a secondary Joule-Thomson orifice connected to a source of compressed gas.

According to further features in preferred embodiments of the invention described below, the Joule-Thomson orifice is shaped and oriented so as to induce in gasses passing therethrough into the first variable volume a motion selected from a group consisting of circular motion, swirling motion, and turbulent motion. The catheter may further comprising a plurality of Joule-Thomson orifices, which may be shaped and oriented so as to induce in gasses passing therethrough into the first variable volume a motion selected from a group consisting of circular motion, swirling motion, and turbulent motion.

According to further features in preferred embodiments of the invention described below, the first variable volume of the first inflatable balloon further comprises a flow control structure designed and constructed to influence circulation of moving gasses within the first variable volume. Preferably, the flow control structure comprises at least one of a group consisting of flow directors for enhancing circular flow, multiple internal channels for subdividing flow, and spoilers for increasing turbulence.

According to further features in preferred embodiments of the invention described below, the catheter further comprises a second inflatable balloon hermetically containing the first inflatable balloon and defining a second variable volume interior to the second inflatable balloon and exterior to the first inflatable balloon, and may comprise a heat-transmitting material contained within the second volume, prefereably selected from a group consisting of a liquid material and a gel material.

According to further features in preferred embodiments of the invention described below, the catheter further comprises a second gas exhaust lumen for exhausting gas from the second volume.

According to further features in preferred embodiments of the invention described below, the catheter further comprises a guide-wire lumen enabling passage of a guide wire through the catheter and an injection lumen suitable for injecting a contrast medium near a distal portion of the catheter.

According to further features in preferred embodiments of the invention described below, the catheter further comprises a moveable thermal sensor operable to report external temperatures at selected positions along a selected length of the catheter, thereby enabling the catheter to report a temperature gradient along a selected segment of a body conduit when the catheter is inserted into the body conduit and the moveable thermal sensor is moved along the catheter. The moveable sensor may be a fiber optic element moveable along the catheter and connectable to a thermographic camera external to the catheter. Alternatively, the catheter further comprises a plurality of thermal sensors operable to report external temperatures along a selected length of the catheter, thereby enabling the catheter to report a temperature gradient along a selected segment of a body conduit when the catheter is inserted into the body conduit. The thermal sensors are preferably selected from a group comprising a thermocouple sensor, a thermographic camera sensor, and a fiber-optic element connectable to a thermographic camera sensor external to the catheter.

According to further features in preferred embodiments of the invention described below, the thermal sensors are spirally configured around and along a section of the catheter, and the catheter further includes a data communication element for communicating data generated by the thermal sensors to a data receiver outside of the catheter. The data communication element may comprise a wire or a wireless communicator.

According to further features in preferred embodiments of the invention described below, at least one of the plurality of thermal sensors comprises a hair-like fiber for enhancing transmission of heat between the at least one sensor and a body tissue adjacent to the sensor.

According to further features in preferred embodiments of the invention described below, the plurality of thermal sensors are distributed along an expandable spiral sensing loop having a distal end anchored to a distal portion of the catheter, the sensing loop being spirally wound around a section of shaft of the catheter and being operable to expand away from the shaft, thereby enhancing thermal communication between the sensors distributed along the sensing loop and body tissues adjacent to the catheter.

The spiral sensing loop may be designed and constructed to expand away from the shaft of the catheter when a proximal end of the sensing loop is pushed toward the anchored distal end of the sensing loop, or be designed and constructed to contract toward the shaft of the catheter when a proximal end of the sensing loop is pulled away from the anchored distal end of the sensing loop.

According to yet another aspect of the present invention there is provided a thermal sensing device designed and constructed to be spirally wrapped around a catheter insertable into a body conduit, the thermal sensing device having a distal end designed and constructed to be anchored to a distal portion of the catheter, the thermal sensing device comprising a plurality of thermal sensors mounted on a spring-like spiral base operable to expand away from the catheter, the expansion enhancing thermal contact between the thermal sensors and tissue of the body conduit, thereby enabling the thermal sensing device to report tissue temperatures along a selected length of the body conduit.

The thermal sensing device of may be designed and constructed to expand away from the catheter when a proximal end of the sensing device is pushed toward the anchored distal end of the sensing device, or designed and constructed to contract towards the catheter when a proximal end of the sensing device is pulled away from the anchored distal end of the sensing device.

According to a further aspect of the present invention there is provided an angioplasty balloon catheter comprising a moveable thermal sensor operable to report external temperatures along a selected length of the catheter, and thereby operable to report a temperature gradient along a selected segment of a body conduit when the catheter is inserted into the conduit and the sensor is moved along the catheter. The moveable sensor may be a fiber optic element moveable along the catheter and connectable to a thermographic camera external to the catheter.

According to yet another aspect of the present invention there is provided an angioplasty balloon catheter comprising a plurality of thermal sensors operable to report external temperatures along a selected length of the catheter, the catheter being operable to report a temperature gradient along a selected segment of a body conduit when the catheter is inserted into the body conduit. The thermal sensors are preferably selected from a group comprising a thermocouple sensor, a thermographic camera sensor, and a fiber-optic element connectable to a thermographic camera sensor external to the catheter, and may be arranged in a spiral configuration around and along a section of the catheter. The catheter may further include a data communication element for communicating data generated by the thermal sensors to a data receiver outside of the catheter. The data communication element may comprise a wire or a wireless communicator.

According to further features in the described preferred embodiments, at least one of the plurality of thermal sensors comprises a hair-like fiber for enhancing transmission of heat between the at least one sensor and a body tissue adjacent to the sensor.

According to still further features in the described preferred embodiments, the plurality of thermal sensors are distributed along an expandable spiral sensing loop having a distal end anchored to a distal portion of the catheter, the sensing loop being spirally wound around a section of shaft of the catheter and being operable to expand away from the shaft, thereby enhancing thermal communication between the sensors distributed along the sensing loop and body tissues adjacent to the catheter.

The spiral sensing loop may be designed and constructed to expand away from the shaft of the catheter when a proximal end of the sensing loop is pushed toward the anchored distal end of the sensing loop. Alternatively, the spiral sensing loop is designed and constructed to contract toward the shaft of the catheter when a proximal end of the sensing loop is pulled away from the anchored distal end of the sensing loop.

According to yet another aspect of the present invention there is provided a system for angioplastic treatment of arterial stenosis and for reducing restenosis, comprising: an angioplasty balloon catheter useable to treat arterial stenosis, having a gas input lumen for supplying a pressurized gas, a first inflatable balloon containing a first variable volume, and a Joule-Thomson orifice for passing the pressurized gas from the gas input lumen into the first variable volume of the first inflatable balloon so as to cool and inflate the first inflatable balloon; a supply of compressed cooling gas operable to supply cooling gas to the gas input lumen; and a cooling gas input valve controlling delivery of compressed cooling gas from the supply of compressed cooling gas to the gas input lumen.

Preferably, the angioplasty balloon catheter further comprises a first gas exhaust lumen for exhausting gas from the first variable volume of the first inflatable balloon, a gas exhaust valve for controlling passage of gas out of the gas exhaust lumen, and a heat exchanging configuration designed and constructed to facilitate transference of heat energy between the gas input lumen and the first gas exhaust lumen.

Preferably, at least a portion of the first gas exhaust lumen is positioned contiguous to at least a portion of the gas input lumen, thereby constituting a heat exchanging configuration. Alternatively, the heat exchanging configuration comprises a section wherein the gas input lumen is positioned within the first gas exhaust lumen, and the gas input lumen, positioned within the first gas exhaust lumen, comprises fins for facilitating heat exchange. Further alternatively, the heat exchanging configuration comprises a section wherein the first gas exhaust lumen is positioned within the gas input lumen and comprises fins for facilitating heat exchange. Further alternatively, the heat exchanging configuration comprises a section wherein the gas input lumen is spirally wrapped around the first gas exhaust lumen, or a section wherein the first gas exhaust lumen is spirally wrapped around the gas input lumen. Further alternatively, the heat exchanging configuration comprises a secondary Joule-Thomson orifice connected to a source of compressed gas.

According to still further features in the described preferred embodiments, the Joule-Thomson orifice is shaped and oriented so as to induce in gasses passing therethrough into the first variable volume a motion selected from a group consisting of circular motion, swirling motion, and turbulent motion.

According to still further features in the described preferred embodiments, the first inflatable balloon further comprises a plurality of Joule-Thomson orifices.

According to still further features in the described preferred embodiments, the first inflatable balloon further comprises a plurality of Joule-Thomson orifices shaped and oriented so as to induce in gasses passing therethrough into the first variable volume a motion selected from a group consisting of circular motion, swirling motion, and turbulent motion.

According to still further features in the described preferred embodiments, the first variable volume of the first inflatable balloon further comprises a flow control structure designed and constructed to influence circulation of moving gasses within the first variable volume.

According to still further features in the described preferred embodiments, the flow control structure comprises at least one of a group consisting of flow directors for enhancing circular flow, multiple internal channels for subdividing flow, and spoilers for increasing turbulence.

According to still further features in the described preferred embodiments, the catheter further comprises a second inflatable balloon hermetically containing the first inflatable balloon and defining a second variable volume interior to the second inflatable balloon and exterior to the first inflatable balloon.

According to still further features in the described preferred embodiments, a heat-transmitting material is contained within the second variable volume, the material selected from a group consisting of a liquid material and a gel material.

According to still further features in the described preferred embodiments, the angioplasty balloon catheter further comprises a guide-wire lumen enabling passage of a guide wire through the catheter.

According to still further features in the described preferred embodiments, the catheter comprises an injection lumen suitable for injecting a contrast medium near a distal portion of the catheter.

This system preferably comprises a second gas exhaust lumen for exhausting gas from the second internal volume, and a helium detector operable to detect presence of helium in the second gas exhaust lumen.

According to still further features in the described preferred embodiments, the system comprises a supply of compressed heating gas operable to supply heating gas to the gas input lumen, and has a heating gas input valve controlling delivery of compressed heating gas from the supply of compressed heating gas to the gas input lumen.

According to still further features in the described preferred embodiments, the system further comprises a supply of a gas mixture comprising compressed cooling gas and compressed heating gas, and has a mixed-gas input valve controlling delivery of mixed gas from the supply of a gas mixture to the gas input lumen. Alternatively, the system has a gas-proportion input valve controlling a ratio of cooling gas to heating gas in the supplied mixture of compressed cooling gas and compressed heating gas.

Preferably, the supply of a gas mixture comprising compressed cooling gas and compressed heating gas is operable to supply a gas which produces no significant thermal effect when passed from a region of high pressure to a region of low pressure through a Joule-Thomson orifice. Preferably, the supply of a gas mixture is operable in a first time to supply a gas which produces no significant thermal effect when passed from a region of high pressure to a region of low pressure through a Joule-Thomson orifice, and further operable in a second time to supply a cooling gas.

According to still further features in the described preferred embodiments, the system further comprises a vacuum pump for rapidly withdrawing gas from the first variable volume of the first inflatable balloon through the first gas exhaust lumen, and/or a vacuum pump for rapidly withdrawing gas from the second internal volume through the second gas exhaust lumen.

According to still further features in the described preferred embodiments, the system further comprises a control unit for controlling functioning of the catheter, the control unit comprising a data collection unit for receiving data generated by at least one sensor positioned in or near a distal portion of the catheter, a processing unit for evaluating data received by the data collection unit according to a stored algorithm, and a command module for sending commands to at least one remotely controlled gas flow valve.

Preferably, the at least one sensor is a thermal sensor.

Preferably, the processing unit comprises a processor and a memory, the memory is operable to record at least a portion of the received data.

Preferably, the processing unit comprises a display operable to display functional data received by the data collection unit.

Preferably, the processing unit is designed and constructed to respond to the received data by evaluating the data under algorithmic control and to generate commands to be sent to at least one remotely controlled gas flow valve based on the evaluation.

Preferably, the control unit is operable to substantially maintain a portion of the catheter near a selected temperature by sending appropriate commands to at least one selected gas flow control valve, the sent commands being chosen according to an algorithm in response to data received from the at least one sensor. Preferably, the at least one selected gas flow control valve is selected from a group comprising a cooling gas input valve, a heating gas input valve, a mixed-gas input valve, and a gas exhaust valve.

According to still further features in the described preferred embodiments, the cooling gas supply further comprises a pre-cooling heat exchanging configuration for pre-cooling supplied cooling gas by exchanging heat between the supplied cooling gas and the gas exhaust lumen.

According to still further features in the described preferred embodiments, the cooling gas supply further comprises a pre-cooling heat exchanging configuration for pre-cooling supplied cooling gas by exchanging heat between the supplied cooling gas and the gas exhaust lumen, and the heating gas supply further comprises a pre-heating heat exchanging configuration, distinct from the pre-cooling heat exchanging configuration, for pre-heating supplied heating gas by exchanging heat between the supplied heating gas and the gas exhaust lumen.

According to still further features in the described preferred embodiments, the system further comprising a direct venting valve enabling venting of gasses from the gas input lumen. Preferably, the direct venting valve being controllable by commands from the command module of the control unit.

According to still further features in the described preferred embodiments, the angioplasty balloon catheter further comprises a moveable thermal sensor operable to report external temperatures at selected positions along a selected length of the catheter, thereby enabling the catheter to report a temperature gradient along a selected segment of a body conduit when the catheter is inserted into the body conduit and the moveable thermal sensor is moved along the catheter.

Preferably, the moveable sensor is a fiber optic element moveable along the catheter and connectable to a thermographic camera external to the catheter.

According to still further features in the described preferred embodiments, the angioplasty balloon catheter further comprises a plurality of thermal sensors operable to report external temperatures along a selected length of the catheter, thereby enabling the catheter to report a temperature gradient along a selected segment of a body conduit when the catheter is inserted into the body conduit. Preferably, the thermal sensors are selected from a group comprising a thermocouple sensor, a thermographic camera sensor, and a fiber-optic element connectable to a thermographic camera sensor external to the catheter. Preferably, the thermal sensors are spirally configured around and along a section of the catheter.

According to still further features in the described preferred embodiments, the system further includes a data communication element for communicating data generated by the thermal sensors to a data receiver outside of the catheter, which data communication element may comprise a wire or a wireless communicator.

According to still further features in the described preferred embodiments, at least one of the plurality of thermal sensors comprises a hair-like fiber for enhancing transmission of heat between the at least one sensor and a body tissue adjacent to the sensor.

According to still further features in the described preferred embodiments, the plurality of thermal sensors are distributed along an expandable spiral sensing loop having a distal end anchored to a distal portion of the catheter, the sensing loop being spirally wound around a section of shaft of the catheter and being operable to expand away from the shaft, thereby enhancing thermal communication between the sensors distributed along the sensing loop and body tissues adjacent to the catheter.

The spiral sensing loop may be designed and constructed to expand away from the shaft of the catheter when a proximal end of the sensing loop is pushed toward the anchored distal end of the sensing loop, or alternatively the spiral sensing loop is designed and constructed to contract toward the shaft of the catheter when a proximal end of the sensing loop is pulled away from the anchored distal end of the sensing loop.

According to still another aspect of the present invention there is provided a method of controlling temperature of gasses passing through a Joule-Thomson orifice, comprising supplying to the Joule-Thomson orifice a gas mixture comprising a pressurized cooling gas and a pressurized heating gas in selected proportion, controlling temperature of gasses passing through the Joule-Thomson orifice by decreasing temperature of gasses passing through the Joule-Thomson orifice by proportionally increasing a ratio of cooling gas to heating gas in the gas mixture, and/or increasing temperature of gasses passing through the Joule-Thomson orifice by proportionally decreasing a ratio of cooling gas to heating gas in the gas mixture. Alternatively, the method comprises pre-mixing the gas mixture, utilizing pressurized heating gas and pressurized cooling gas in a selected proportion.

Preferably, the method further comprises utilizing an automated control unit to select a ratio of cooling gas to heating gas in the gas mixture by receiving temperature data from a thermal sensor in a vicinity of the Joule-Thomson orifice, and sending control signals to at least one remotely controllable gas flow valve in response to an algorithmic evaluation of the received temperature data, thereby modifying the selected ratio of cooling gas to heating gas in the gas mixture.

According to still another aspect of the present invention there is provided a method of reducing restenosis after angioplasty, comprising inflating an inflatable angioplasty balloon with cooling gas supplied by a high-pressure source of cooling gas passed through a Joule-Thomson orifice, thereby cooling and inflating the angioplasty balloon, thereby cooling arterial tissues adjacent to the balloon during angioplasty, thereby reducing restenosis.

According to yet another aspect of the present invention there is provided a method of reducing restenosis after angioplasty, comprising performing angioplasty by inflating an inflatable angioplasty balloon a gas which neither substantially cools nor substantially heats the during inflation, balloon, and cooling the inflated angioplasty balloon by circulating therein a gas cooled by passage through a Joule-Thomson orifice, thereby cooling arterial tissues adjacent to the balloon subsequent to angioplasty, thereby reducing restenosis.

According to still another aspect of the present invention there is provided a method providing for safety testing of an angioplasty balloon catheter having a first inflatable balloon containing a first variable volume, a gas input lumen operable to introduce gas into the first variable volume, a second inflatable balloon hermetically containing the first inflatable balloon and defining a second variable volume interior to the second inflatable balloon and exterior to the first inflatable balloon, and a gas exhaust lumen providing free exit to gas within the second variable volume, comprising introducing a gas into the first variable volume through the gas input lumen, and utilizing a gas detector to detect presence of the introduced gas in the gas exhaust lumen, thereby determining whether the introduced gas has leaked, through a failure of the first inflatable balloon, from the first variable volume into the second variable volume. Preferably, the introduced gas is helium gas, and the gas detector is a detector of helium gas. Preferably, the method further comprises testing of the first inflatable balloon prior to an angioplasty operation, thereby verifying integrity of the first inflatable balloon prior to using the angioplasty balloon catheter in a surgical procedure, thereby contributing to safety of the surgical procedure.

According to still another aspect of the present invention there is provided a method providing for safe use of an angioplasty balloon catheter having a first inflatable balloon having a first variable volume, a gas input lumen operable to introduce gas into the first variable volume, a Joule-Thomson orifice useable to cool gasses introduced into the first inflatable balloon, a second inflatable balloon hermetically containing the first inflatable balloon and defining a second variable volume interior to the second inflatable balloon and exterior to the first inflatable balloon, and a gas exhaust lumen providing free exit to gas within the second variable volume, comprising the steps of a) utilizing a gas mixture of pressurized cooling gas and a relatively smaller amount of an additional gas to cool the first inflatable balloon during an angioplasty procedure, and b) utilizing a gas detector to monitor gas in the gas exhaust lumen to detect a presence of the additional gas in the gas exhaust lumen, and c) ceasing all supply of pressurized gas to the gas supply lumen if presence of the additional gas is detected in the gas exhaust lumen, thereby providing for safe use of the angioplasty balloon catheter by reducing danger of leakage of gas from the catheter into surrounding tissues. Preferably, the additional gas is helium, and the gas detector is a detector of helium gas. Preferably, the method further comprises utilizing a vacuum pump to rapidly exhaust all gasses from the angioplasty balloon catheter if a gas leak is detected.

According to still another aspect of the present invention there is provided a method of accurately positioning an angioplasty balloon catheter for an angioplasty procedure, the method comprising a) introducing into an artery the angioplasty balloon catheter, the angioplasty balloon catheter having an inflatable balloon operable to perform angioplasty and a plurality of temperature sensors arranged along a selected section of the catheter, b) manipulating the catheter into a selected segment of the artery suspected of having an aflicted portion, c) operating the temperature sensors to determine temperatures at a plurality of sites along the selected segment of the artery, d) comparing the temperature readings to determine a locus, within the section of the artery, having a temperatures high than those measured within other portions of the artery, and e) further manipulating the catheter so as to position the balloon in a vicinity of the determined locus, thereby accurately positioning the angioplasty balloon catheter for the angioplasty procedure.

According to still another aspect of the present invention there is provided a method of treating a stenotic inflammation of an artery, comprising: a) introducing into an artery an angioplasty balloon catheter having an inflatable balloon operable to perform angioplasty and a plurality of temperature sensors arranged along a selected section of the catheter, b) manipulating the catheter into a selected segment of the artery suspected of having an inflamed portion, c) operating the temperature sensors to determine temperatures at a plurality of sites along the selected segment of the artery, d) comparing the temperature readings to determine a locus, within the section of the artery, having a temperatures high than those measured within other portions of the artery, e) further manipulating the catheter so as to position the balloon in a vicinity of the determined locus, and f) inflating the balloon so as to compress tissues around the balloon at the locus, thereby performing angioplasty, thereby treating the stenotic inflammation of the artery.

The present invention successfully addresses the shortcomings of the presently known configurations by providing an apparatus and method of cooling an angioplasty balloon enabling rapid cooling and optional rapid heating of an angioplasty balloon, and further enabling accurate, rapid, and exact control of temperatures within that balloon and/or within the treated body tissues.

The present invention further successfully addresses the shortcomings of the presently known configurations by providing an apparatus and method of cryogenic cooling in an angioplasty balloon catheter that provides for exact control of temperature within a balloon in a manner relatively independent of the dilation pressure maintained within that balloon.

The present invention further successfully addresses the shortcomings of the presently known configurations by providing apparatus and method of cryogenic cooling of the balloon of an angioplasty balloon catheter, which method and apparatus provide for accurate control of temperature of the balloon during cooling, and further provide a highly evenly distribution of cold throughout that balloon catheter.

The present invention further successfully addresses the shortcomings of the presently known configurations by providing a system for detecting a leak in a balloon angioplasty system, which detection is highly sensitive to even very small leaks in an inner angioplasty balloon, thereby enabling to immediately cease supply of input fluids, and to undertake other or additional corrective measures, as soon as such a very small leak is detected, and without necessitating waiting for a leak large enough to significantly raise pressure in an outer balloon volume.

The present invention further successfully addresses the shortcomings of the presently known configurations by providing apparatus and method enabling accurate placement of an angioplasty balloon catheter based information garnered at a potential intervention site by an angioplasty balloon catheter, in real time.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 2A, 2B, and 2C, are simplified schematics presenting additional optional features of the angioplasty balloon catheter presented in FIG. 1A., according to an embodiment of the present invention;

FIGS. 3A and 3B are simplified schematics illustrating alternate constructions for heat exchanging configurations useable within a angioplasty balloon catheter, according to an embodiment of the present invention;

FIGS. 4A and 4B are simplified schematics illustrating use of stents with a cryocatheter, according to an embodiment of the present invention;

FIG. 13 is a simplified schematic presenting a cryocatheter comprising an injection lumen and a guide-wire lumen, according to an embodiment of the present invention;

FIG. 14 is a simplified schematic presenting an alternate positioning for a guide wire lumen within a cryocatheter, according to an embodiment of the present invention;

FIG. 25 is a simplified schematic of another alternative construction for a section of an angioplasty balloon catheter enabling multiple temperature measurements along a selected section of an artery, according to an embodiment of the present invention.

DESCRIPTION OF THE PREFERRED EMBODIMENTS

Figure 1A:
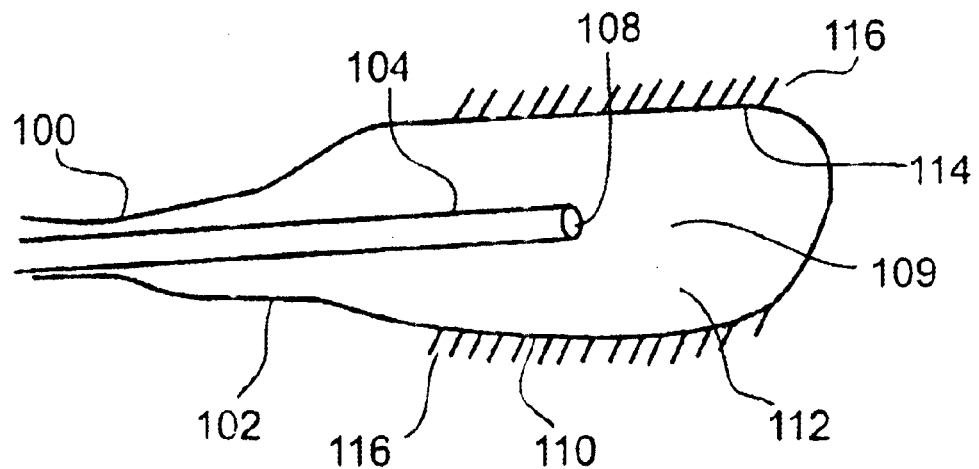
FIGS. 1A and 1B are simplified schematics illustrating alternate basic schemes for constructing an angioplasty balloon catheter useable to treat arterial stenosis, utilizing Joule-Thomson cooling, according to an embodiment of the present invention.

The present invention is of an angioplasty balloon catheter operable to utilize compressed gas for direct Joule-Thomson cooling of an angioplasty balloon with a high degree of temperature control, and having a plurality of temperature sensors operable to measure temperatures at a variety of locations within an artery, thereby providing information permitting to identify a locus for placement of an angioplasty balloon for treatment of arterial stenosis.

Specifically, the present invention can be used to accurately place an angioplasty balloon in a position appropriate for balloon angioplasty treatment of stenosis, and to directly cool an angioplasty balloon during use in treatment of stenosis, thereby discouraging or preventing restenosis.

The principles and operation of a cryogenic angioplasty balloon catheter according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

To enhance clarity of the following descriptions, the following terms and phrases will first be defined:

The phrase "heat-exchanging configuration" is used herein to refer to component configurations traditionally known as "heat exchangers", namely configurations of components situated in such a manner as to facilitate the passage of heat from one component to another. Examples of "heat-exchanging configurations" of components include a porous matrix used to facilitate heat exchange between components, a structure integrating a tunnel within a porous matrix, a structure including a coiled conduit within a porous matrix, a structure including a first conduit coiled around a second conduit, a structure including one conduit within another conduit, or any similar structure.

The phrase "Joule-Thomson heat exchanger" as used herein refers, in general, to any device used for cryogenic cooling or for heating, in which a gas is passed from a first region of the device, wherein it is held under higher pressure, to a second region of the device, wherein it is enabled to expand to lower pressure. A Joule-Thomson heat exchanger may be a simple conduit, or it may include an orifice through which gas passes from the first, higher pressure, region of the device to the second, lower pressure, region of the device. A Joule-Thomson heat exchanger may further include a heat-exchanging configuration, for example a heat-exchanging configuration used to cool gasses within a first region of the device, prior to their expansion into a second region of the device.

The phrase "cooling gasses" is used herein to refer to gasses which have the property of becoming colder when passed through a Joule-Thomson heat exchanger. As is well known in the art, when gasses such as argon, nitrogen, air, krypton, $CO_2$, $CF_4$, xenon, and $N_2O$, and various other gasses pass from a region of higher pressure to a region of lower pressure in a Joule-Thomson heat exchanger, these gasses cool and may to some extent liquefy, creating a cryogenic pool of liquefied gas. This process cools the Joule-Thomson heat exchanger itself, and also cools any thermally conductive materials in contact therewith. A gas having the property of becoming colder when passing through a Joule-Thomson heat exchanger is referred to as a "cooling gas" in the following.

Other gasses have the property of becoming hotter when passed through a Joule-Thomson heat exchanger. Helium is an example of a gas having this property. When helium passes from a region of higher pressure to a region of lower pressure, it is heated as a result. Thus, passing helium through a Joule-Thomson heat exchanger has the effect of causing the helium to heat, thereby heating the Joule-Thomson heat exchanger itself and also heating any thermally conductive materials in contact therewith. Helium and other gasses having this property are referred to as "heating gasses" in the following.

As used herein, a "Joule Thomson cooler" is a Joule Thomson heat exchanger used for cooling. As used herein, a "Joule Thomson heater" is a Joule Thomson heat exchanger used for heating.

As used herein, the term "angioplasty" is used to refer in particular to balloon angioplasty.

As used herein, the term "cryoplasty" is used to refer to angioplasty in which standard angioplasty procedures are supplemented by cooling of treated tissues, either during angioplasty or subsequent to angioplasty.

In discussion of the various figures described hereinbelow, like numbers refer to like parts.

Referring now to the drawings, FIG. 1A is a simplified schematic illustrating a basic schemes for constructing an angioplasty balloon catheter useable to treat arterial stenosis, utilizing Joule-Thomson cooling, according to an embodiment of the present invention. Such a catheter is sometimes referred to as a "cryocatheter" in the following.

Figure 1B:
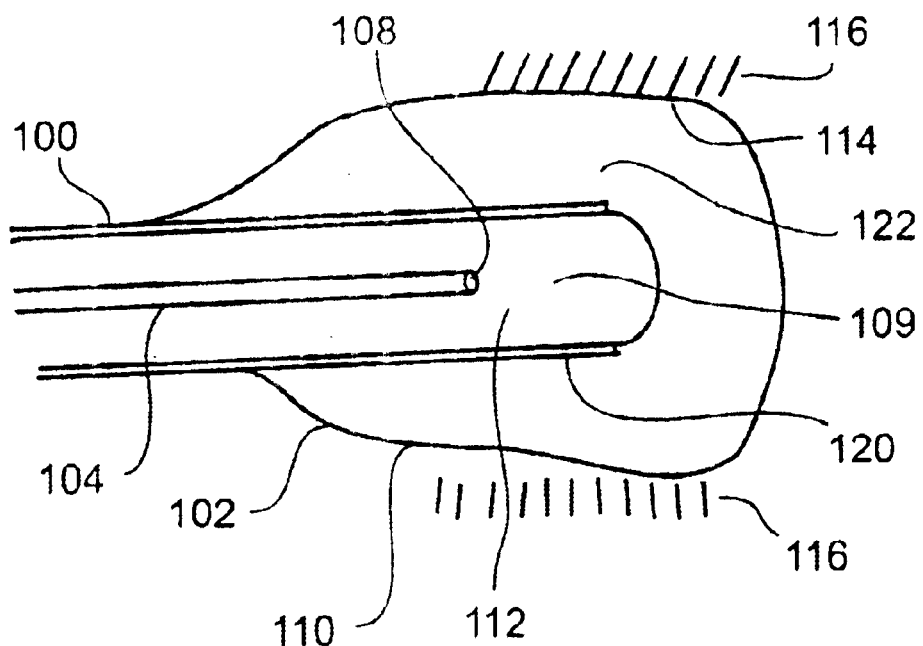

Elements common to FIGS. 1A and 1B include an angioplasty balloon catheter 100, of which distal portion 102 is shown, a gas input lumen 104 for providing pressurized gas from a pressurized gas source to distal portion 102, and a balloon 110 having a variable volume 112 capable of holding a gas under pressure. In typical use, catheter 100 is introduced into an artery or other body conduit or body cavity with balloon 110 in compressed or compacted form, the reduced diameter of balloon 110 facilitating its insertion into the blood vessel or other cavity or conduit. Subsequently, balloon 110 is expanded by introduction of pressurized gas into variable volume 112, thereby directly or indirectly transferring pressure to surrounding tissues.

Referring now to the configuration presented by FIG. 1A, pressurized gas supplied through gas input lumen 104 into volume 112 of balloon 110 causes balloon 110 to expand. Expansion of balloon 110 brings wall 114 of balloon 110 into contact with surrounding tissues.

In typical use, catheter 100 is placed in an artery having a region requiring angioplasty therapy, and then pressurized gas is supplied to volume 112, causing balloon 110 to expand and forcing external walls of balloon 110 into contact with tissues 116 surrounding catheter 100, and exerting pressure on those tissues. Pressure thus induced by balloon 110 on tissues 116 surrounding balloon 110 constitutes an angioplasty intervention.

In a preferred embodiment, gas input lumen 104 terminates in a Joule-Thomson orifice 108. When gas supplied though gas input lumen 104 is a cooling gas as defined hereinabove, there results a combined effect in which gas entering volume 112 is both pressurized, thereby expanding balloon 110, and cold, thereby cooling balloon 110. Thus, the combination of elements consisting of gas input lumen 104 supplying pressurized gas through orifice 108 into lower-pressure volume 112 constitutes a Joule-Thomson heat exchanger 109 as defined hereinabove.

Balloon 110 is preferably constructed of a thermally conductive material, hence cooling an inner face of wall 114 of balloon 110 has the effect of cooling an outer face of wall 114, thereby cooling body tissues 116 external to, but in close proximity to, or in contact with, balloon 110.

Balloon 110 is preferably constructed of one or more (preferably two) layers of thin plastic material such as PVC or PET (polyester), or polyethylene tetphthalate or nylon, or similar material. Thus, balloon 110 may be constructed of material similar or identical to the materials composing commercially available in PTA (percutaneous translumenal angioplasty) and PTCA (percutaneous translumenal coronary angioplasty) systems, such as those sold, for example, by Cordis Inc., Guidant Inc., Advanced Polymers Inc., and others. Thickness of balloon wall 114 is preferably between 1 and 100 microns, and most preferably between 5 and 50 microns.

Gas input lumen 104, designed to contain and transport high-pressure gas, is preferably constructed of high strength flexible metal such as stainless steel or Cupro-Nickel, or of high strength plastic tubing.

All parts of catheter 100 are constructed of non-toxic biocompatible materials.

FIG. 1A presents a presently preferred construction, in which cooling gas from input lumen 104, having expanded and cooled, directly cools balloon 110. FIG. 1B presents an alternative construction, in which volume 112 is further contained within a tube 120, preferably constructed of plastic or metal, and tube 120 is further contained in a heat-transmission layer 122, preferably containing a liquid or a gel.

The construction presented by FIG. 1A has the advantage of enabling greater miniaturization of catheter 110, a more rapid cooling process, better cooling power per unit area, and a more rapid balloon response time during inflation and deflation.

An advantage of the construction presented by FIG. 1B is that it is more easily implemented than the construction presented in FIG. 1A, and can more easily be demonstrated to be safe to use.

Figure 2C:
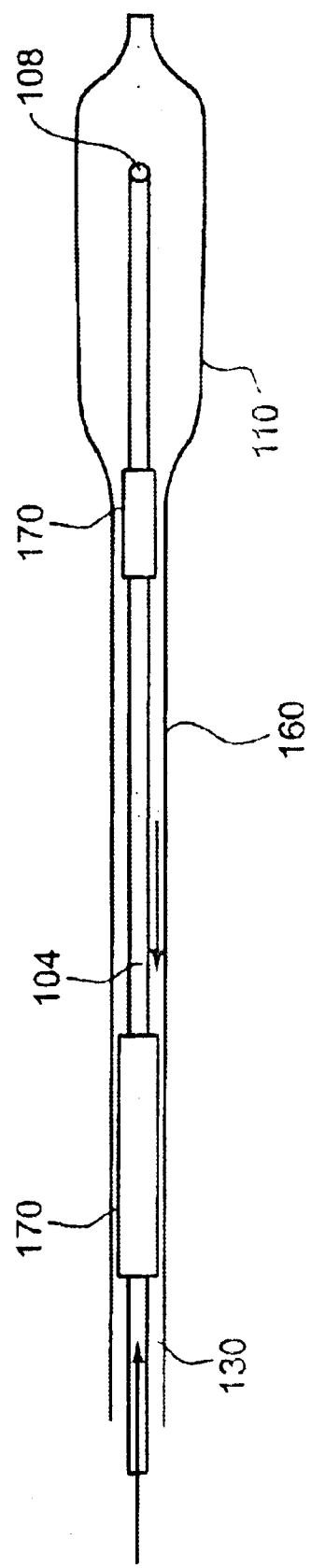

Attention is now drawn to FIGS. 2A and 2B and 2C, which are simplified schematics presenting additional optional features the an angioplasty balloon catheter presented in FIG. 1A, according to an embodiment of the present invention.

Common to FIGS. 2A, 2B, and 2C is a flexible tube 160 containing contains gas supply lumen 104 and gas exhaust lumen 130. Flexible tube 160 flexibly connects distal portion 102 of catheter 100, containing balloon 110, to a supply of compressed gasses and to various control mechanisms for controlling supply of compressed gas. Tube 160 is sufficiently flexible to be insertable into a body conduit such as an artery, and to be operable to follow the natural path of that conduit during insertion.

FIG. 2A presents a gas exhaust lumen 130, for voiding gas from volume 112. In a preferred embodiment, passage of gas from gas exhaust lumen 130 is controlled by a gas exhaust control valve 132, which may be a manual valve or a remotely-controlled valve controllable by commands from an electronic control module 150.

In a preferred construction, gas exhaust lumen 130 is in close physical contact with gas input lumen 104, so as to facilitate exchange of heat between input gas contained in gas input lumen 104 and exhaust gas contained in gas exhaust lumen 130. In a particularly preferred construction shown in FIG. 2A, gas input lumen 104 is largely contained within gas exhaust lumen 130, thereby constituting a heat exchanging configuration as defined hereinabove, facilitating heat exchange between the two lumens. Thus, during a cooling process, cold exhaust gas in gas exhaust lumen 130 pre-cools input gas in gas input lumen 104, thereby enhancing the cooling effect of Joule-Thomson heat exchanger 109.

In an alternate preferred construction, a portion of gas exhaust lumen 130 may be contained within a portion of gas input lumen 104, similarly constituting a heat exchanging configuration for enhancing heat exchange between lumens 104 and 130.

In a further alternate construction, lumens 104 and 130 are contiguous and touching over a portion of their length. Such a construction also constitutes a heat exchanging configuration serving to enhance heat exchange between lumens 104 and 130.

Further alternate constructions providing heat exchanging configurations for pre-cooling and/or pre-heating input gasses are presented hereinbelow.

FIG. 2B presents at least one internal heat sensor 140 within catheter 100. In a preferred embodiment, catheter 100 comprises a plurality of heat sensors 140 distributed throughout catheter 100. Sensor 140 may be a thermocouple 142 or other heat-sensing device, such as a thermographic camera, or a fiber-optic fiber operable to transfer infrared radiation to a thermographic camera or other heat sensor external to catheter 100. Heat sensor 140 may be connected by wire to an external control module 150, or may alternatively be connected through a wireless data link, such as a radio link, to control module 150. Control module 150 may have a variety of monitoring, reporting, and control functions, as will be explained in further detail hereinbelow.

FIG. 2C presents heat exchanging configurations 170 optionally installed in one or more sections of catheter 100, to facilitate and enhance heat exchange between input gas lumen 104 and exhaust gas lumen 130. The functionality and desirability of such a transfer of heat has been explained hereinabove. Various methods for constructing heat exchanging configurations 170 are well known in the art. One popular example is a spiral configuration, which might be implemented in catheter 100 by having gas input lumen 104 spirally wrapped around gas exhaust lumen 130, or by having gas exhaust lumen 130 spirally wrapped around gas input lumen 104, or by having both lumens spirally wrapped around each other, these constructions each serving to increase a surface of contact between the two lumens so as to facilitate exchange of heat between them, thereby pre-cooling cooling gas prior to its arrival at Joule-Thomson orifice 108, or alternatively pre-heating heating gas prior to its arrival at Joule-Thomson orifice 108.

Heat exchanging configurations 170 may be optionally installed at various positions along flexible tube 160, or at the interface between flexible tube 160 and distal portion 102, or yet in various positions within a system supplying high-pressure gas to catheter 100 (not shown). Use of dedicated heat exchanging configurations 170 is optional. A construction such as that presented in FIG. 2A, in which input gas lumen 104 is positioned within exhaust gas lumen 130 over some portion of its length, is in itself a heat exchanging configuration, and may in some implementations provide sufficient heat exchanging activity so that no further dedicated heat exchanging configurations 170 are required.

Attention is now drawn to FIGS. 3A and 3B, which are simplified schematics illustrating additional alternate constructions for heat exchanging configurations 170. FIG. 3A presents a heat exchanging configuration wherein a first gas lumen 163 is positioned within a second gas lumen 165, and the first gas lumen presents fins 176 to enhance heat exchange between the gasses contained in lumens 163 and 165. As indicated in the figure, such a heat exchanging configuration can be implemented with gas input lumen 104 as inner lumen 163 and exhaust gas lumen 130 as outer lumen 165. As further indicated in the figure, such a heat exchanging configuration can alternatively be implemented with exhaust gas lumen 130 as inner lumen 163 and input gas lumen 104 as outer lumen 165.

FIG. 3B presents yet another heat exchanging configuration, in which, secondary gas input lumen 177 and a secondary Joule-Thomson orifice 178 have been added to a configuration otherwise similar to that presented in FIG. 3A. The configuration presented by FIG. 3B might be used, for example, to further enhance pre-cooling of cooling gas in gas input lumen 104, by combining pre-cooling power of cold exhaust gasses from gas exhaust lumen 130 with additional pre-cooling power of additional pressurized cooling gas supplied through secondary gas input lumen 177 and expanded on passing through Joule-Thomson orifice 178. Supply of gas to secondary gas input lumen 177, if used, is preferably controlled through a remotely controlled valve under control of control module 150, described in detail hereinbelow.

Heat exchanging configurations as illustrated in FIGS. 3A and 3B may optionally be used as heat exchanging configurations 170 presented in FIG. 2C, or at other locations within catheter 100 or within a gas supply module supplying pressurized gas to catheter 100.

In operation of catheter 100, high pressure incoming gas is supplied to catheter 100 from a gas supply module operable to supply cooling gas and preferably also operable to supply heating gas. Incoming gas is preferably initially supplied at or near room temperature, and is preferably supplied at a pressure between 2000 to 6000 psi, and most preferably at a pressure between 3000 to 4500 psi. Incoming gas flows through input gas lumen 104 and expands through the orifice 108 inside the balloon 110.

If the incoming gas is a cooling gas, temperate of this input gas is reduced drastically through the Joule-Thomson effect as it passes into balloon 110, reaching a temperature preferably between 0 C. and −186 C., and more preferably between −90 C. and −140 C. Attainable temperatures on the surface of balloon 110, in contact with body tissue, are between −10 C. and −80 C. Attainable temperature gradients for freezing and thawing are up to 100 C. per second.

Cold gas having served to cool balloon 110 flows out of balloon 110 and into gas exhaust lumen 130, where it is preferably used to cool incoming gas in input gas lumen 104, as described above.

As shown in FIG. 2A, gas exhaust control valve 132 is operable to control pressure of exhaust gasses flowing out of balloon 110. Appropriate manipulation of valve 132 enables to maintain a desired pressure within balloon 110, preferably between 3 and 50 atmospheres of pressure, and more preferably between 6 and 27 atmospheres.

Valve 132 may be implemented as a manual valve, yet valve 132 is preferably implemented as a remotely controlled valve under control of control system 150. Control system 150 is preferably operable to control flow of exhaust gas through valve 132. Control system 150 is further operable to control flow of input gasses to balloon 110, as will be shown hereinbelow. Combined control of input of gas into balloon 110 and output of exhaust gas from balloon 110 enables control module 150 to establish and maintain a desired pressure within balloon 110, or indeed to establish an maintain a desired pressure profile over time, according to a pre-planned treatment profile or to real-time preferences of an operator responding to real-time requirements of a therapeutic procedure.

Attention is now drawn to FIGS. 4A and 4B, which are simplified schematics illustrating the use of stents with cryocatheter 100, according to an embodiment of the present invention.

FIG. 4A shows a catheter 100 whose balloon 110 is deflated and is covered by a stent 174 in collapsed configuration. In a preferred embodiment, diameter of distal portion 102 of catheter 100, including deflated balloon and collapsed stent 174, is not substantially greater than that of flexible tube 160, enabling distal portion 102 to pass easily along an artery or other body conduit. As shown in FIG. 4B, when distal portion 102 has been appropriately positioned in proximity to tissues to be treated, cooling gasses or other gasses may be used to inflate balloon 110, thereby performing angioplasty, optionally positioning stent 174 in expanded configuration within an artery or other body conduit, and optionally cooling surrounding tissues to discourage restenosis. Balloon 110 is preferably inflated with cooling gasses so as to cool treated tissues as they are compressed by the angioplasty balloon, yet alternatively balloon 110 may be inflated with non-cooling gasses or with a liquid. Similarly, if it is desired to heat balloon 110, for example to facilitate disengagement of catheter 110, such heating is preferably accomplished by supplying compressed heating gas through input gas lumen 104 through orifice 108 into balloon 110, yet heating may alternatively be accomplished by supplying low-pressure pre-heated gasses other than heating gasses, or further alternatively, heating may be accomplished by supplying a heated liquid through input lumen 104.

Figure 5:
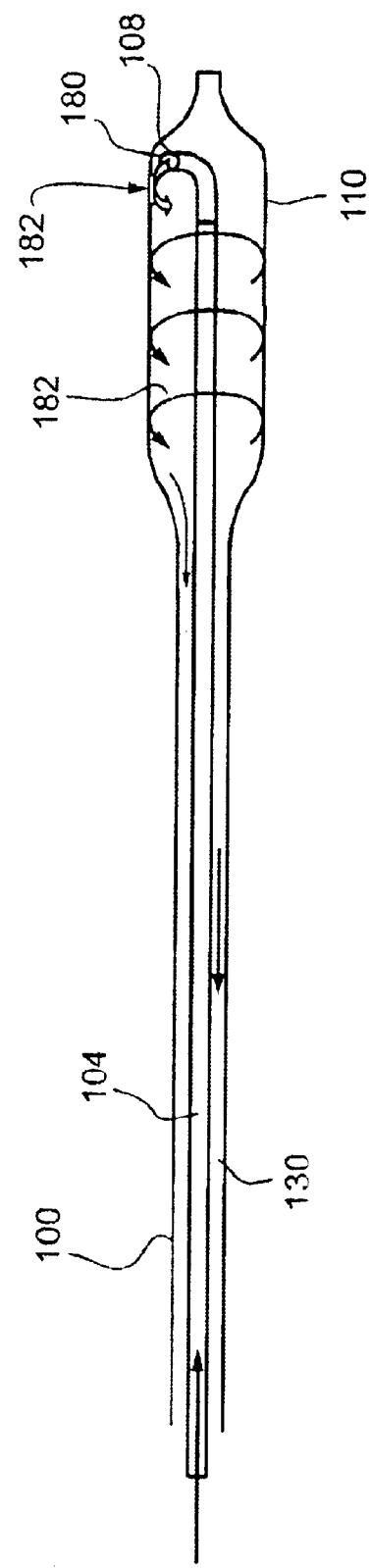
FIG. 5 is a simplified schematic of a cryocatheter having a Joule-Thomson orifice so shaped and oriented as to induce selected patterns of motion in gasses passing therethrough, according to an embodiment of the present invention.

Attention is now drawn to FIG. 5, which is a simplified schematic of a cryocatheter having a Joule-Thomson orifice shaped and oriented so as to induce selected patterns of motion in gasses passing therethrough, according to an embodiment of the present invention.

As shown in FIG. 5, high-pressure gas from gas input lumen 104 passes through Joule-Thomson orifice 108 into balloon 110. Orifice 108 is formed as a shaped nozzle 180 designed and constructed to induce a selected form of motion in gas passing therethrough, as indicated by arrows 182. Shaped nozzle 180 may be oriented in a manner which directs gasses passing therethrough to circulate within balloon in a circular motion pattern, or alternately in a manner which directs gasses passing therethrough to circulate within balloon 110 in a swirling or spiral pattern. Shaped nozzle 180 may, for example, be placed near an interior wall of balloon 110 and be oriented tangentially to that wall. Further alternately, shaped nozzle 180 may be formed in a shape that deflects gas flow, or nozzle 180 may comprise obstructive shapes which induce turbulence in gasses passing therethrough into balloon 110.

As discussed in the background section hereinabove, one disadvantage of certain prior art systems is the uneven cooling produced, wherein parts of an angioplasty balloon which are proximate to the delivery site of evaporative cooling fluid tend to be much colder than other areas of that angioplasty balloon. The configuration illustrated by FIG. 5 can be used to reduce or eliminate uneven cooling, by directing gas cooled by expansion upon exit from Joule-Thomson orifice 108 to circulate effectively within balloon 110, thereby enhancing heat transfer between cold gas and interior walls of balloon 110, thereby contributing to relatively even cooling throughout all of balloon 110.

Alternatively, the configuration illustrated by FIG. 5 can be used to produce intentionally uneven cooling by concentrating cooling within a selected area of balloon 110. Shaped nozzle 180 can be formed and oriented in a manner which directs a concentrated flow of cold gas into a selected portion of balloon 110, thereby enhancing cooling in that selected portion, leaving higher temperatures in other areas of balloon 110.

Figure 6:
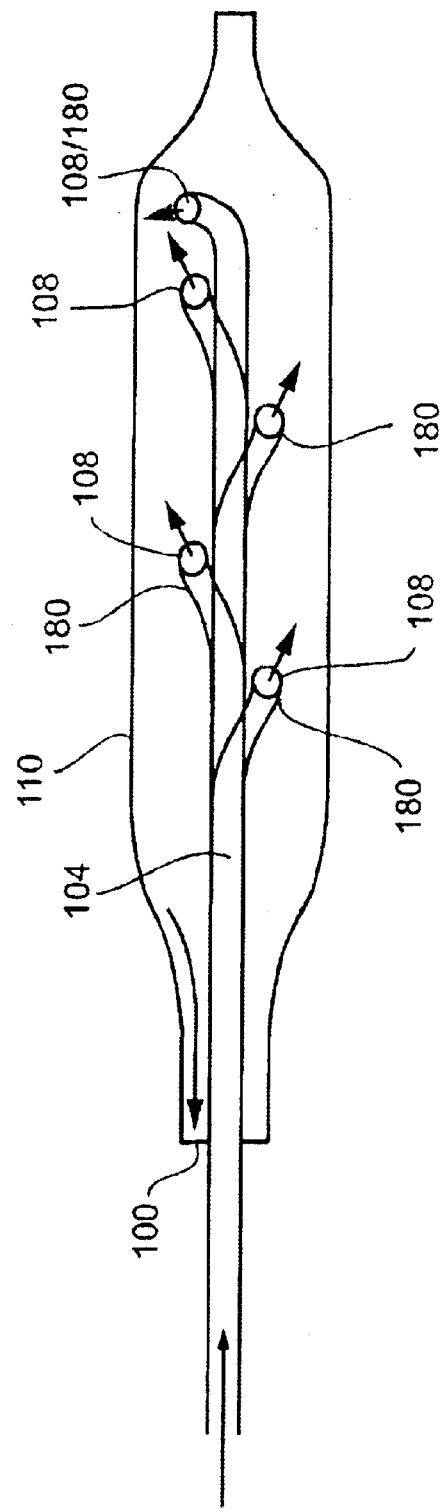
FIG. 6 is a simplified schematic of a cryocatheter comprising a plurality of Joule-Thomson orifices, according to an embodiment of the present invention.

Attention is now drawn to FIG. 6, which is a simplified schematic of a cryocatheter comprising a plurality of Joule-Thomson orifices, according to an embodiment of the present invention. As illustrated in FIG. 6, a catheter 100 comprises a plurality of Joule-Thomson orifices 108, some or all of which may be formed and oriented as shaped nozzles 180 designed and constructed to induce a selected form of motion in gas passing therethrough. The configuration presented in FIG. 6 may be used to ensure good circulation of cool gas within balloon 110 so as to enhance even distribution of cooling throughout balloon 110. Alternatively, a configuration similar to that presented in FIG. 6, but wherein a plurality of orifices 108 are concentrated in a selected area of balloon 110 and distanced from other parts of balloon 110, may be utilized to concentrate cooling in a selected portion of balloon 110, and to lessen the degree of cooling in non-selected portions of balloon 110.

Figure 7:
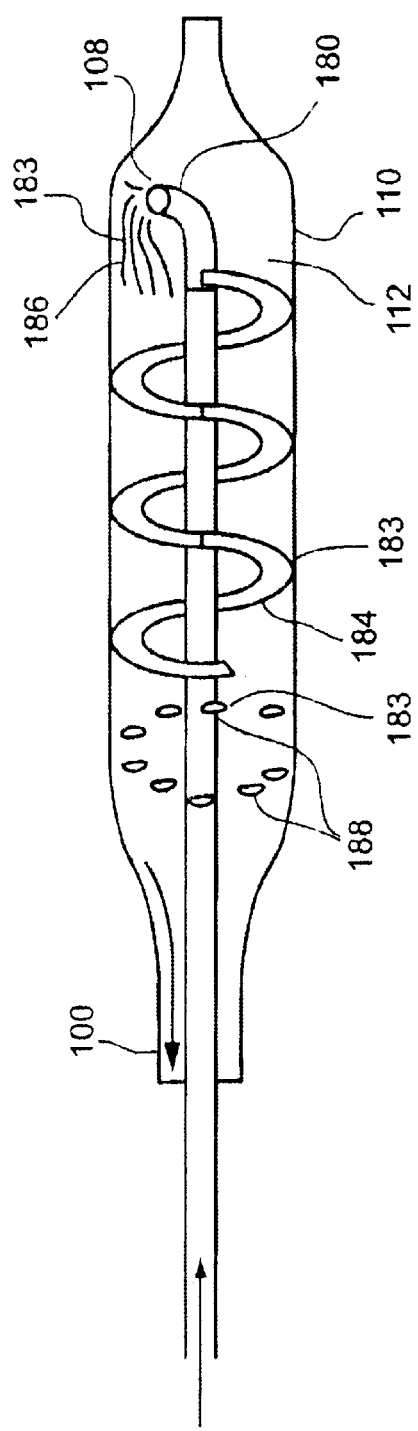
FIG. 7 is a simplified schematic of a cryocatheter comprising flow control structures for directing a flow of gas within an angioplasty balloon, according to an embodiment of the present invention.

Attention is now drawn to FIG. 7, which is a simplified schematic of a cryocatheter comprising flow control structures for directing a flow of gas within an angioplasty balloon, according to an embodiment of the present invention. As was shown above with respect to FIGS. 5 and 6, selected number, placement, shape, and orientation of gas delivery orifices 108 can produce a configuration which enhances even distribution of cooling gas throughout balloon 110, or alternatively can be used to produce a configuration which concentrates cooling in a selected portion of balloon 110. FIG. 7 presents an alternative (or complementary) configuration useable to enhance evenly distributed cooling or, alternatively, to achieve selectively concentrated cooling.

FIG. 7 presents a catheter 100 wherein interior volume 112 of balloon 110 comprises flow control structures 183 designed and constructed to influence circulation of moving gasses within volume 112. Several forms of flow control structures are presented.

Flow directors 184 guide gasses into a desired pattern of motion. For example, flow directors 184 may be used to enhance circular flow of gas, or spiral flow of gas.

Multiple internal channels 186 serve to subdivide gas flow.

Spoilers 188 serve to increasing turbulence of circulating gas.

Flow control structures 183 are preferably constructed of material identical to, or similar to, materials of which balloon 110 is constructed.

Figure 8:
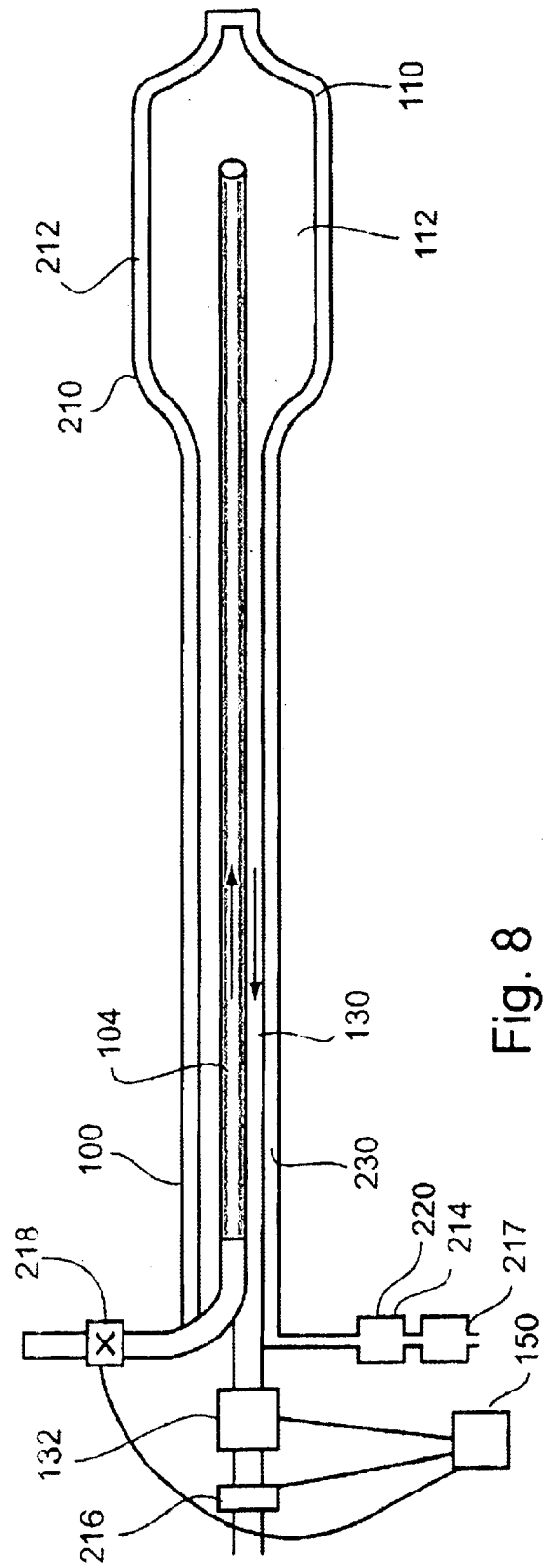
FIG. 8 is a simplified schematic of a cryocatheter comprising two inflatable balloons, according to an embodiment of the present invention.

Attention is now drawn to FIG. 8, which is a simplified schematic of a cryocatheter 100 comprising two inflatable balloons, according to an embodiment of the present invention. FIG. 8 presents a preferred embodiment, in which a first inflatable balloon 110 defining a first variable volume 112 is hermetically contained within a second inflatable balloon 210 defining a second variable volume 212 interior to second inflatable balloon 210 and exterior to first inflatable balloon 110.

One possible use of the configuration presented in FIG. 8 is to fill or partially fill second variable volume 212 with a heat-transmitting material, such as a liquid, semi-liquid, or gel material, thus producing a configuration similar to that described hereinabove with reference to FIG. 1B.

In a currently preferred embodiment, volume 212 is not filling with heat-transmitting material, but rather is left unfilled. A second gas exhaust lumen 230 in fluid communication with second variable volume 212 is operable to exhaust gas from volume 212.

A gas detector 214 is operable to detected presence of gas in volume 212. In use, volume 212 is initially free of gas, and no gas is intentionally input therein, consequently if gas detector 214 detects presence of gas from volume 212, such detection may be taken as an indication that pressurized gas from volume 112 has leaked into volume 212 through a hole or fault in balloon 110. In a preferred implementation, detection of gas under such circumstances is reported to a control unit 150, which may then undertake such measures as to command gas exhaust valve 132 to release pressure from balloon 110, command a first emergency gas exhaust pump 216 to pump all gas from balloon 110, command a gas input valve 218 to cease supplying gas to gas input lumen 104, and command a second emergency gas exhaust pump 217 to pump all gas from balloon 210. Optionally, first and second emergency gas exhaust pumps 216 and 217 can be implemented as a single common pump.

Gas detector 214 may be a detector of gas pressure, as used in prior art devices. Yet in a particularly preferred embodiment of the present invention, gas detector 214 is a helium gas detector, operable to detect presence of helium gas. Helium detectors are available having extreme sensitivity to presence of even very small quantities of helium gas, even to quantities on the order of only a few PPM. Varian Inc., for example, manufactures such a helium detector. Consequently, use of a helium detector 220 as gas detector 214 has significant advantages, in that it allows detection of even very tiny leaks in balloon 110, when balloon 110 contains any concentration of helium gas. Thus, if gas detector 214 is implemented as helium detector 220, and balloon 110 contains at least a small concentration of helium gas, the system illustrated by FIG. 8 is able to detect and respond to extremely small gas leaks in balloon 110, and in particular is able to respond to leaks which would likely go undetected if gas detector 214 were merely a detector of rising gas pressure in volume 212. Thus, use of helium detector 220 in the configuration presented in FIG. 8 contributes significantly to enhancing safety of use of catheter 100. The configuration presented in FIG. 8 may similarly be utilized as a leak detection and response system for angioplasty balloon systems incorporating catheters of other types.

The leak detection system illustrated by FIG. 8 may be used in a variety of ways. One preferred method of use is to test catheter 100 prior to use for angioplasty or cryogenic cooling, by introducing a small amount of helium gas into balloon 110 prior to inflating balloon 110 with cooling gas or any other fluid. As stated, the extreme sensitivity of available helium detectors 220 ensures that, if even a small amount of low-pressure helium is introduced into balloon 110, a fault or leak in balloon 110 will be detectable by detector 220.

A currently preferred method of maintaining operational safety of catheter 100 is to mix a selected portion of helium gas with cooling gas, or with any other fluid used to inflate balloon 110, not only prior to inflating balloon 110, but also during normal inflation and cooling operations of catheter 100 as well. According to this preferred method, at least a small amount of helium gas is added to whatever cooling gas or other fluid is used to inflate balloon 110. The extreme sensitivity of available helium detectors 220 ensures that even a small leak of helium will permit leak detection, even when the amount of helium added to a fluid (e.g., a cooling gas) supplied to balloon 110 is sufficiently small to have little or no substantial effect on the gas temperature obtained when such a gas mixture passes from a high pressure area to a low pressure area through Joule-Thomson orifice 108. Thus, utilizing a cooling gas containing at least a small portion of helium gas, and utilizing a helium gas detector 220 as illustrated, enables to detect leaks or faults in balloon 110 with a high degree of precision and during the entire course of an angioplasty and/or cryoplasty procedure, thus greatly enhancing the safety of such a procedure.

Figure 9:
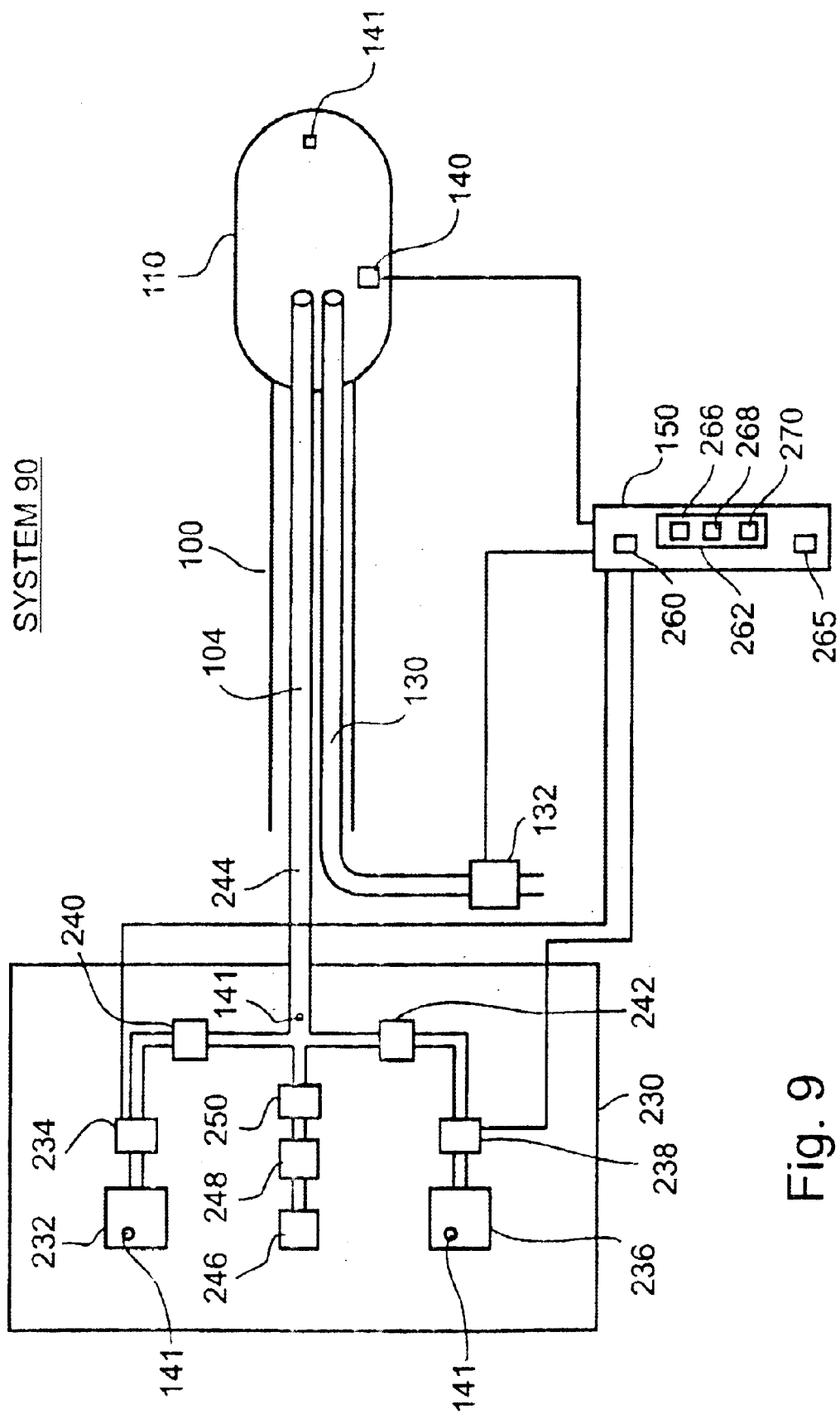
FIG. 9 is a simplified schematic of a system comprising a cryocatheter and apparatus for controlling operating temperatures thereof, according to an embodiment of the present invention.

Attention is now drawn to FIG. 9, which is a simplified schematic of a system comprising a cryocatheter and apparatus for controlling operating temperatures thereof, according to an embodiment of the present invention.

FIG. 9 presents a system 90 for angioplastic treatment of arterial stenosis and for reducing restenosis.

System 90 comprises an angioplasty balloon catheter 100 useable to treat arterial stenosis, catheter 100 having a gas input lumen 104 for supplying a pressurized gas, a first inflatable balloon 110 containing a first variable volume 112, and a Joule-Thomson orifice 108 for passing pressurized gas from gas input lumen 104 into first variable volume 112 of first inflatable balloon 110 so as to cool and inflate balloon 110.

System 90 further comprises a supply of compressed cooling gas 232 operable to supply cooling gas to gas input lumen 104, and a cooling gas input valve 234 controlling delivery of compressed cooling gas from compressed cooling gas supply 232 to gas input lumen 104.

System 90 further comprises a first gas exhaust lumen 130 for exhausting gas from first variable volume 112 of balloon 110, and a gas exhaust valve 132 for controlling passage of gas out of gas exhaust lumen 130.

System 90 further comprises a supply of compressed heating gas 236 operable to supply heating gas to gas input lumen 104, and a heating gas input valve 238 controlling delivery of compressed heating gas from compressed heating gas supply 236 to gas input lumen 104.

Gas supplies 232 and 236, input valves 234 and 238, and one-way valves 240 and 242, together constitute a gas supply module 230. Gas supply module 230 is operable to supply compressed cooling gas, to supply compressed heating gas, and to supply a mixture containing both compressed cooling gas and compressed heating gas. Valves 234 and 238 together constitute a mixed-gas input valve system operable to control delivery of mixed gas from gas supply module 230 to gas input lumen 104, and further operable to control the ratio of cooling gas to heating gas in a mixed gas supplied to gas input lumen 104. In an alternative construction, valves 234 and 238 may be combined into a proportional valve governing the proportion of cooling gas to heating gas delivered to gas input lumen 104.

In an alternative construction, a pre-mixed compressed gas supply 246, flow from which is controlled by a pre-mixed gas input valve 248, may also supply gas, through a one-way valve 250, to gas input lumen 104. Pre-mixed compressed gas supply 246 contains a mixture of cooling gas and heating gas in selected proportion. Mixed gas supply 246 may be used instead of, or in conjunction with, cooling gas supply 232 and heating gas supply 236.

Mixing a heating gas, such as helium, with a cooling gas can provide a useful service, over an above the gas-leak detection service described hereinabove with reference to FIG. 8. As mentioned in the background section hereinabove, in various surgical procedures, and particularly in treatment of arterial stenosis, optimal temperature for treatment of afflicted tissues can be somewhat less cold than the maximum cooling temperature which can be achieved by a cryocatheter cooled by Joule-Thomson cooling. In practice, it is desirable that a surgeon be enabled to exercise control over the operating temperature of catheter 100, so that he or she can select an appropriate temperature for each therapeutic situation. Indeed, it is further desirable to enable a surgeon to specify a temperature profile defined over time, permitting him or her to specify, for example, an initial temperature to be maintained during a first selected period, followed by a second temperature to be maintained during a second selected period, perhaps followed by a heating cycle used during disengagement of catheter 100.

It is noted that gas supply module 230, operable to supply a mixture of heating and cooling gas, is operable to supply a gas having a mixture of heating and cooling gasses selected in such proportion that little or no substantial heating or cooling effect results when a compressed gas mixture so selected passes through a Joule-Thomson orifice. Gas supply module 230 can thus be used to provide a gas operable to inflate balloon 110 without significantly heating it nor cooling it. According to a preferred embodiment of the present invention, system 90 is operable to supply such a non-heating non-cooling mixture to balloon 110 during a first time, so as to perform angioplasty without cooling, and then subsequently to supply a cooling gas mixture to balloon 110 during a second time, so as to cool treated tissues subsequent to, rather than simultaneously with, compression of those tissues by angioplasty. Of course, in alternate preferred embodiments, cooling and angioplasty may be practiced simultaneously, as variously described herein.

It is to be noted that various valves illustrated in FIG. 9 as controlling gas flow into and out of balloon 110 are preferably remotely controllable by commands from control module 150. Gas exhaust valve 132, useable to control gas flow through gas exhaust lumen 130, is preferably controllable by control module 150. Cooling gas input valve 234 controlling flow of cooling gas from gas supply module 230, and heating gas input valve 238 controlling gas flow from heating gas source 236, are preferably controllable by control module 150. Thus, flow of gas passed by cooling gas input valve 234 and one-way valve 240, through gas input lumen 104 and thence through orifice 108 into balloon 110, and flow of gas passed by heating gas input valve 236 and one-way valve 242, through gas input lumen 104 and thence through orifice 108 into balloon 110, are both controllable by control module 150.

Control module 150 is preferably operable to control input valves 234 and 238 according to operator commands, or alternatively according to programmed commands stored in a memory, or further alternatively according to algorithmic calculations made according to programmed commands and applied to data received from sensors such as sensors 140.

Thus, gas supply module 230 is operable to supply cooling gas to gas input lumen 104 when so desired, and to supply heating gas to gas input lumen 104 when so desired. A gas input module so configured is well known in cryosurgery practice, where it has typically been used to provide alternating cooling and heating to cryoprobes in cryoablation systems, where it accepted practice to cool a probe to effect cryoablation, and subsequently to heat that probe after cryoablation to free it from tissues to which a freezing process has caused it to adhere.

The configuration presented in FIG. 9 enables, however, a new and different use of gas supply module 230. According to a preferred method of operation of the configuration here presented, cooling gas input valve 234 and heating gas input valve 238 are operable to provide both cooling gas and heating gas to input gas lumen 104 simultaneously or nearly simultaneously, so as to obtain in input gas lumen 104 a mixture 244, which mixture is comprised of cooling and heating gasses in selected proportion. The effect of passing such pressurized mixture 244 of heating and cooling gasses through orifice 108 is to produce a cooling or heating effect in which the degree of cooling or of heating obtained is finely controllable. Increasing the proportion of cooling gas in mixture 244 will increase the cooling effect. Decreasing the proportion of cooling gas in mixture 244 will decrease the cooling effect.

Management of mixture 244 is preferably controlled by control module 150, issuing commands to valves 234, 238, and optionally 248, which commands are determined under algorithmic control based on calculations made on a basis of data in form of real-time temperature information received from one or more heat sensors 140 positioned within balloon 110, or positioned in other portions of the body of catheter 100, or positioned in tissue areas proximate to catheter 100, and optionally further based on data from pressure sensors 141 placed in various positions within system 90.

Control module 150 can thus operate a feedback control cycle, in which temperature changes registered by sensors 140 and reported to control module 150 cause control module 150 to command changes in relative amounts of gas passed by cooling gas valve 234 and heating gas valve 238, thereby enabling control module 150 to establish fine control of temperatures in and around catheter 100 during operation.

It is to be noted that system 90 enables fine control of temperature, which control is relatively independent of quantities of gas passing orifice 108, in that a desired cooling effect can be created by using a relatively small gas flow composed preponderantly of cooling gas, or by using a relatively large flow of gas composed of relatively less cooling gas and somewhat more heating gas.

This relative independence of the cooling effect from the absolute amount of gas flow is particularly useful in the context of angioplastic therapy, since it enables a surgeon, preferably through use of control services provided by control module 150, to independently manipulate pressure maintained in balloon 110 on the one hand, and temperature maintained in balloon 110 on the other hand.

Control module 150 provides various control and monitoring functions for the system presented in FIG. 9. Control module 150 preferably comprises a data collection unit 260 for receiving data generated by at least one sensor positioned in or near a distal portion of catheter 100, such as thermal sensors 140 and pressure sensors 141. Control module 150 preferably further comprises a processing unit 262 for evaluating data received by data collection unit 260 according to a stored algorithm 264, and a command module 265 for sending commands to one or more remotely controlled gas flow valves, such as valves 234, 248, 238, and 132.

Processing unit 262 preferably comprises a processor 266 and a memory 268, memory 268 being operable to record at least a portion of data received by data collection unit 260. Processing unit 262 optionally comprises a display 270 operable to display functional data received by data collection unit 260.

Processing unit 262 is preferably designed and constructed to respond to received data, to evaluate it under algorithmic control, to generate commands based on these algorithmically controlled evaluations, and to send commands so generated to valves 234, 248, 238, 132, and to other valves and remotely controllable units within system 90.

As described hereinabove, in a preferred embodiment control unit 150 is operable to substantially maintain a portion of catheter 100 near a selected temperature, by sending appropriate commands to at least one, and preferably more than one, gas flow control valve, using commands chosen according to an algorithm in response to data received from sensor 140, and preferably from a plurality of sensors, including thermal sensors and pressure sensors.

In an optional preferred embodiment, system 90 may be implemented utilizing as catheter 100 a double-balloon catheter such as that discussed hereinabove with reference to FIG. 8. In such an embodiment, gas detector 214 (preferably helium detector 220), integrated into system 90, is operable to report detection of gas (preferably detection of helium) to control module 150. Command module 150, upon receipt of a report of gas detection by detector 214, is operable to command actions by emergency vacuum pumps 216 and 217 and gas input valve 218, according to a programmed response pattern.

In an additional optional preferred embodiment, system 90 may also be implemented utilizing, in place of cryocatheter 100, a cryoablation probe designed and constructed for cryoablation of tumors. A system so constructed, utilizing mixed gas 244 to provide fine control of degree of cooling as explained hereinabove, may be used to advantage in cryoablation applications in which less-than-maximal cooling of a cryoprobe is desired for clinical reasons.

Figure 10:
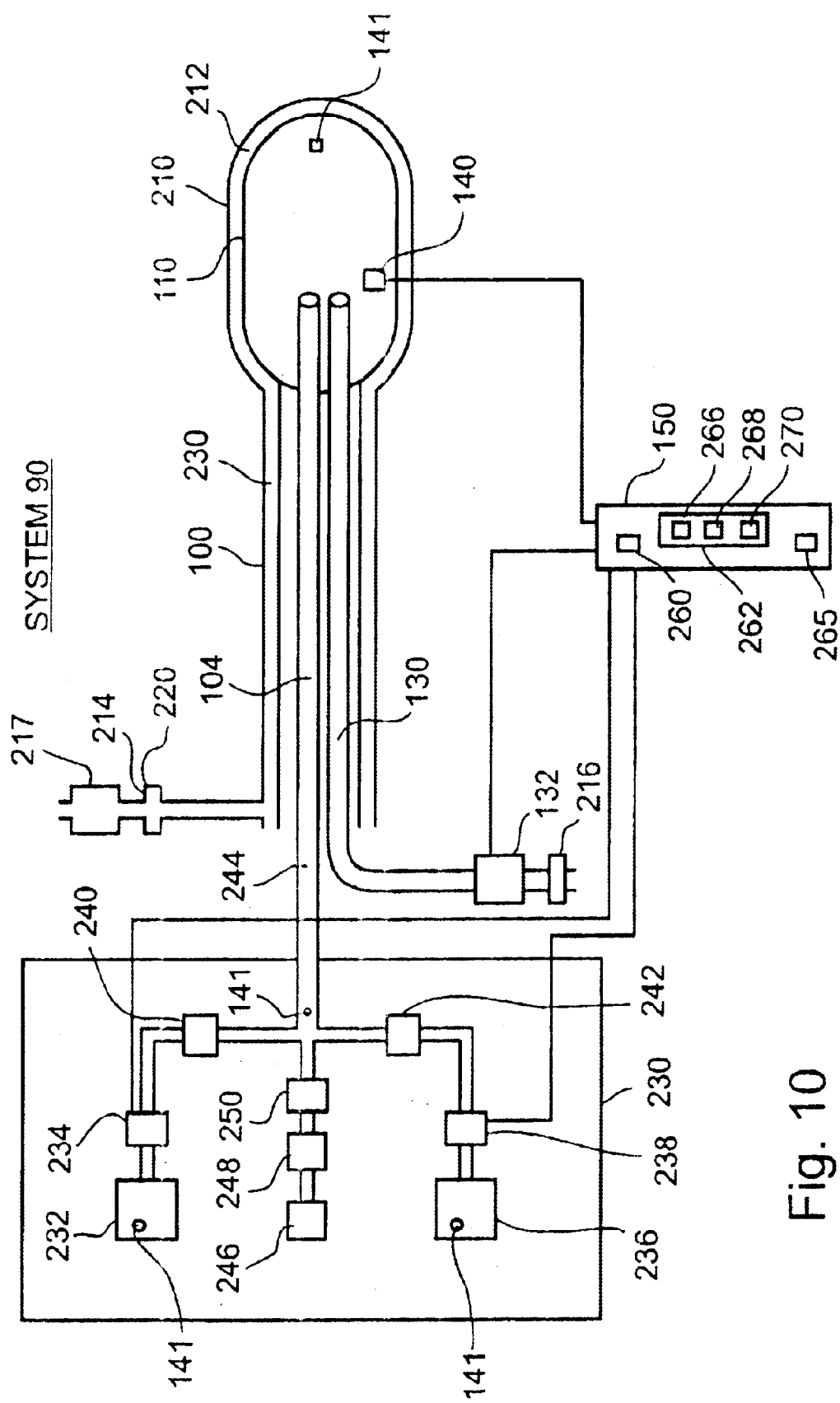
FIG. 10 is a simplified schematic presenting a system comprising an apparatus for detecting and for responding to gas leaks in an inner balloon of a double-balloon catheter, according to an embodiment of the present invention.

Attention is now drawn to FIG. 10, which is a simplified schematic presenting an embodiment of system 90 comprising a double-balloon catheter 100, and apparatus for detecting and for responding to gas leaks in inner balloon 110. The system presented in FIG. 10 may be seen to include the various characteristics of system 90 as described hereinabove with respect to FIG. 9, and to further included the double-balloon catheter, gas leak detection mechanism, and gas leak response apparatus described hereinabove with respect to FIG. 8.

Figure 11:
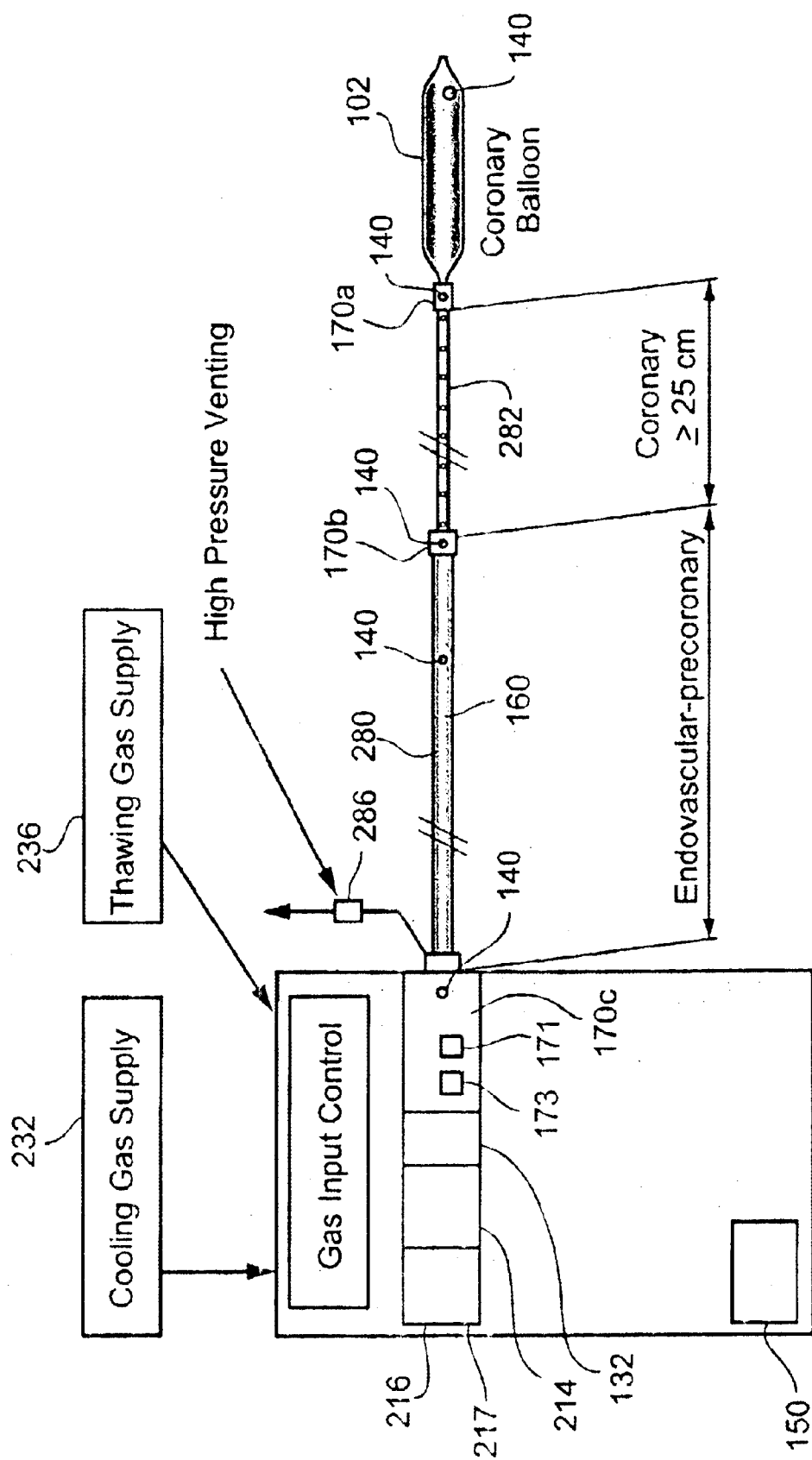
FIG. 11 is a simplified schematic presenting an optional alternate construction for a cryocatheter system including several heat exchanging configurations, according to an embodiment of the present invention.

Attention is now drawn to FIG. 11, which is a simplified schematic presenting an optional alternate construction for system 90, according to an embodiment of the present invention. The system illustrated in FIG. 11 is distinguished by the presence of heat exchanging configurations 170 in a plurality of functional positions within the system.

In FIG. 11, system 90 has been conceptually subdivided into one external and three internal units.

Gas supply module 230, containing mechanisms for gas supply and gas input control, for helium detection and leak control, and for emergency vacuum pumping, is external to the patient's body.

Catheter 100, designed for insertion into the body, is conceptually divided into three sections. Endovascular-precoronary section 280 comprises flexible tube 160, designed to be flexibly inserted into a blood vessel or other bodily conduit of a patient. Coronary section 282, preferably about 25 cm in length, is designed to enter the coronary region of the body during an angioplasty procedure. Distal portion 102 consists primarily of inflatable balloon 110, and optional second inflatable balloon 210.

As shown in FIG. 10, heat exchanging configurations 170 may be utilized in various areas, to enhance the efficiency with which cryogenic cooling is accomplished. Heat exchanging configuration 170A is placed at a point of transition between coronary section 282 and distal portion 102. Heat exchanging configuration 170B is placed at a point of transition between coronary section 282 and endovascular-precoronary section 280. Other emplacements for heat exchanging configurations 170, within sections 280, 282 and 102, may also be used.

Another optional placement for a heat exchanging configuration 170 is shown in FIG. 11 as heat exchanging configuration 170C. Heat exchanging configuration 170C is an integrated component of gas supply module 230, and thus is positioned outside the body during operation.

Each of the heat exchanging configurations 170A, 170B, and 170C is operable to exchange heat between exhaust gas from exhaust gas lumen 130 and input gas within, or flowing towards, input gas lumen 104. Additional heating and cooling systems may be utilized in addition to, or in place of, one or more heat exchanging configurations 170. In particular, a pre-cooling system 171 may be used in addition to, or in place of, heat exchanging configuration 170C, within gas supply module 230, utilizing electrical cooling, a closed refrigeration cycle, a liquid nitrogen bath, liquid nitrogen secondary flow, or other similar methods.

Alternate gas heating methods may also be used to provide heat to catheter 100. An electrically heated low-pressure gas supply 173 may be so used. Units 171 and 173, if used, are preferably controlled by control unit 150.

Optional high-pressure vent 286 is provided, preferably near a coupling between gas supply module 230 and cryocatheter 100, for selectively venting gas from input lumen 104. Use of vent 286 may be useful in a variety of circumstances. During an emergency such as detection of a gas leak in balloon 110, it may be desirable to immediately reduce pressure in balloon 110. Additionally, a desired rapid change of operating temperature within balloon 110, for example a change from a cooling phase of operation to a heating phase of operation, is best accomplished by venting pressurized gas of one type (e.g., cooling gas) in input lumen 104, before starting to supply gas of a second type (e.g., heating gas) to input lumen 104. High-pressure vent 286 is preferably controlled by control module 150.

Each heat exchanging configuration 170 is preferably equipped with a thermal sensor 140 operable to report operating temperatures to control module 150. Additional thermal sensors 140 may be positioned at other sites within catheter 100, or indeed at additional sites external to catheter 100, such as within gas supply module 230, or within body tissues of a patient in proximity to catheter 100.

Figure 12:
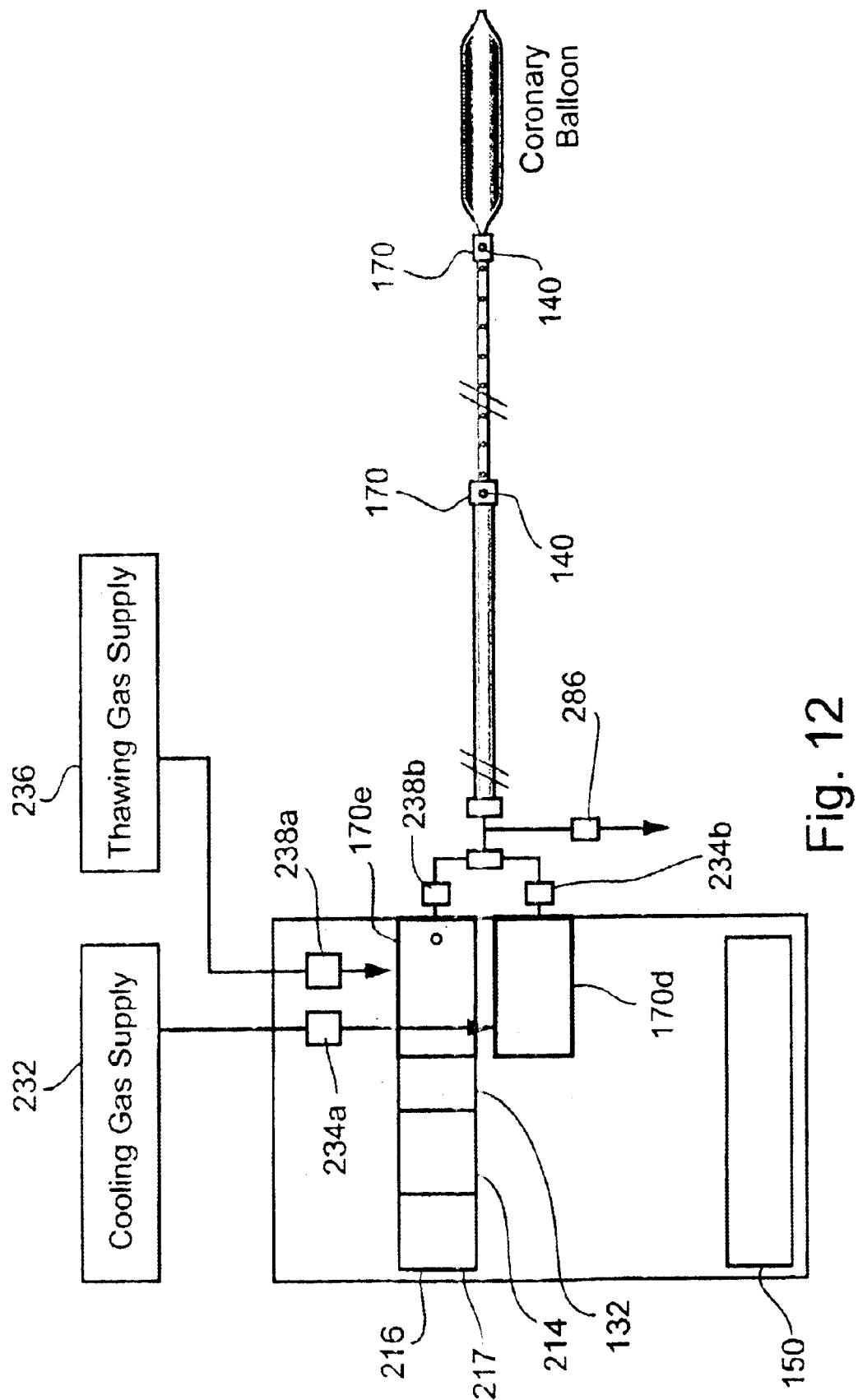
FIG. 12 is a simplified schematic presenting an alternate configuration for a cryocatheter system, including separate heat exchanging configurations for cooling gas and for heating gas, according to an embodiment of the present invention.

Attention is now drawn to FIG. 12, which presents an additional alternate configuration for system 90. FIG. 12 features separate heat exchanging configurations 170D and 170E in place of heat exchanging configuration 170C of FIG. 11. Heat exchanging configuration 170D is operable to pre-cool cooling gas from cooling gas supply 232 on its way to input gas lumen 104, preferably using exhausted cold gas from gas exhaust lumen 130. Heat exchanging configuration 170E is operable to pre-heat heating gas from heating gas supply 236 on its way to input gas lumen 104, using exhausted hot gas from gas exhaust lumen 130. Heat exchanging configurations 170D and 170E may optionally be constructed according to configurations described hereinabove with reference to FIGS. 3A and 3B.

Input valves controlling input of cooling gas may be placed at position 234A or at position 234B, or in both positions. Input valves controlling input of heating gas may be placed at position 238A or at position 238B, or in both positions.

The configuration presented by FIG. 12 is useful because efficient heat exchange, in heat exchanging configurations 170C, 170D, and 170E, requires a relatively large internal volume of gas within those heat exchanging configurations. Using a common heat exchanging configuration 170C both to pre-cool cooling gas and to pre-heat heating gas, as is done in the configuration presented by FIG. 11, has an effect of reducing speed of response of system 90 to a change from a first gas input (e.g., cooling gas) to a second gas input (e.g., heating gas), since a relatively large volume of a first gas must be flushed from heat exchanging configuration 170C before heat exchanging configuration 170C can be entirely filled with, and dedicated to the pre-cooling or pre-heating of, an intended second gas.

A more rapid response to a change from cooling to heating, or from heating to cooling, maybe obtained from the configuration presented in FIG. 12, wherein each gas source has a dedicated heat exchanging configuration, 170D dedicated to pre-cooling cooling gas, and 170E dedicated to pre-heating heating gas. Input valves 234A and/or 234B and 238A and/or 238B need merely be closed and opened appropriately, to produce an almost immediate response from gas supply module 230, with no delay required for flushing the system of inappropriate gas.

Attention is now drawn to FIG. 13, which is a simplified schematic presenting additional features of a cryocatheter according to an embodiment of the present invention.

FIG. 13 presents a catheter 100 comprising an optional injection lumen 290 suitable for injecting a material near distal portion 102 of catheter 100. Injection lumen 290 is useful for injecting, for example, a contrast imaging material into are area near a treatment site, to facilitate imaging of that site, thereby facilitating correct placement of catheter 100 for treatment, or thereby facilitating evaluation of an ongoing or completed angioplasty procedure.

FIG. 13 further presents a guide-wire lumen 292 for enabling and guiding passage of a guide wire through a length of catheter 100. According to a common surgical practice, a guide wire is often used to guide insertion of an angioplasty catheter during an angioplasty procedure. Guide wire lumen 292 serves to permit passage of a guide wire 294 along an internal length of catheter 100, providing compatibility with standard wire-guided angioplasty procedures.

Attention is now drawn to FIG. 14, which is a simplified schematic presenting an alternate positioning for a guide wire lumen within a cryocatheter, according to an embodiment of the present invention. Whereas guide wire lumen 292 presented in FIG. 13 is centered within catheter 100 and particularly within balloon 110, circumferential guide wire lumen 296 presented in FIG. 14 has a circumferential positioning within balloon 110. Such circumferential positioning permits guide wire lumen 296, and within it guide wire 294, to be embedded within wall 114 of balloon 110, for example between adjacent layers of material forming wall 114.

Figure 15A:
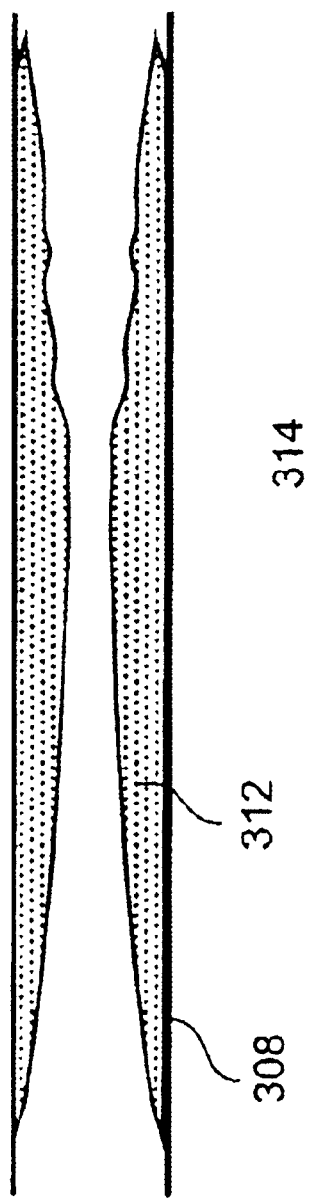
FIGS. 15A, 15B, and 15C illustrate, in simplified form, clinical findings pertaining to a relationship between temperature of tissues lining a coronary artery and stenotic narrowing of that artery due to plaque.
Figure 15B:
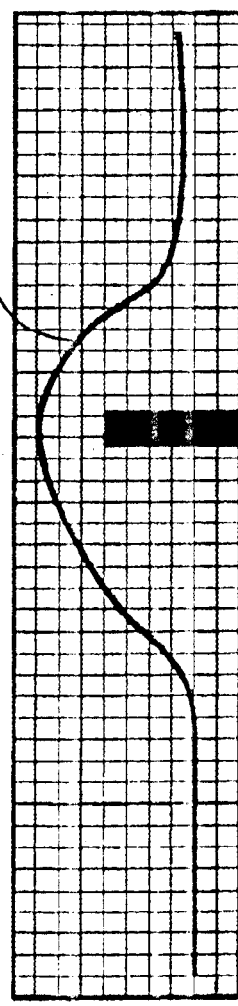
Figure 15C:
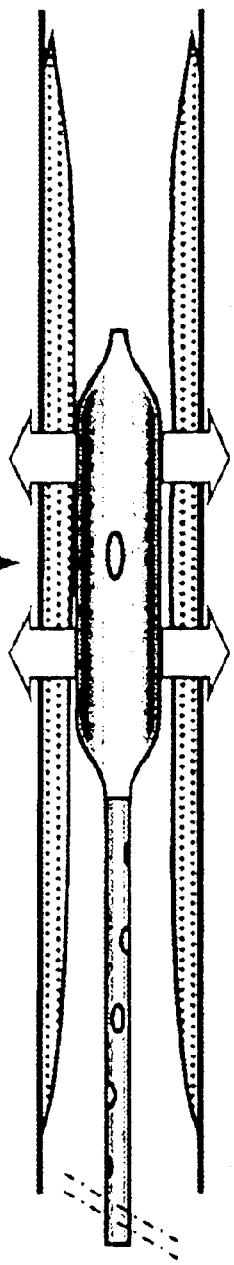

Attention is now drawn to FIGS. 15A, 15B, and 15C, which illustrate in simplified form clinical findings of a relationship often found to obtain between temperature of tissues lining a coronary artery and stenotic narrowing of arteries due to plaque.

FIG. 15A schematically illustrates a section of coronary artery 308 in which blood flow is impeded by a narrowing, caused by plaque 312.

FIG. 15B presents a temperature graph 314 of coronary artery section 308, where temperature is plotted on a vertical axis against position plotted on a horizontal axis, the horizontal axis being common to FIGS. 15A, 15B, and 15C. FIG. 15B presents a well-known clinical finding, that areas narrowed by plaque tend to have a higher temperature than other, healthier, areas within a same arterial section. This temperature differential, apparently resulting from an inflamed state of tissues at the site of the restriction, may be used to localize that restriction for treatment. FIG. 15C shows a balloon catheter (e.g., catheter 100) appropriately positioned for treating the condition seen in FIG. 15A and localized by temperature chart 15B.

Figure 16:
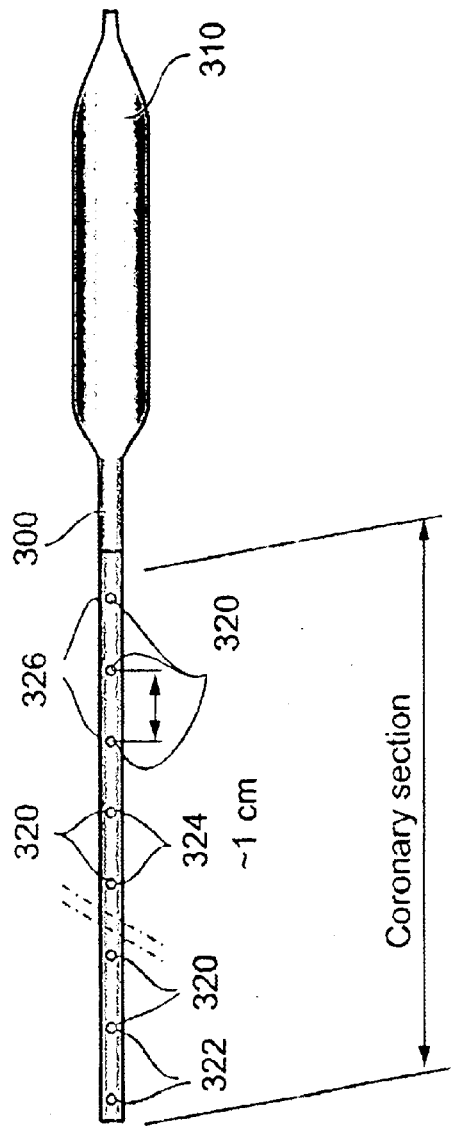
FIG. 16 is a simplified schematic of an angioplasty balloon catheter comprising a plurality of external temperature sensors, according to an embodiment of the present invention.

Attention is now drawn to FIG. 16, which is a simplified schematic of an angioplasty balloon catheter comprising a plurality of external temperature sensors located along a selected section thereof, according to an embodiment of the present invention.

In FIG. 16, angioplasty balloon catheter 300 comprises an inflatable balloon 310 operable to perform angioplasty, and a plurality of temperature sensors 320 (also called "thermal sensors" and "heat sensors" in the following) arranged along a selected section of catheter 300. Catheter 300 may have the characteristics of catheter 100 described hereinabove, or alternatively may be a cryogenic balloon catheter coolable using methods of prior art, or further alternatively may be a cryogenic balloon catheter coolable using other methods of cooling, or yet further alternatively catheter 300 may be an angioplastic balloon catheter not comprising mechanisms for cooling balloon 310.

Temperature sensors 320 may be thermocouples 322, or thermographic camera sensors 324, or fiber-optic fibers 326 operable to transmit infra-red light from a tissue site to a thermographic camera sensor 324 external to catheter 300, or any other sensor operable to report temperatures in a vicinity of body tissues in proximity to catheter 300, when catheter 300 is inserted in an artery or other body conduit.

Figure 17:
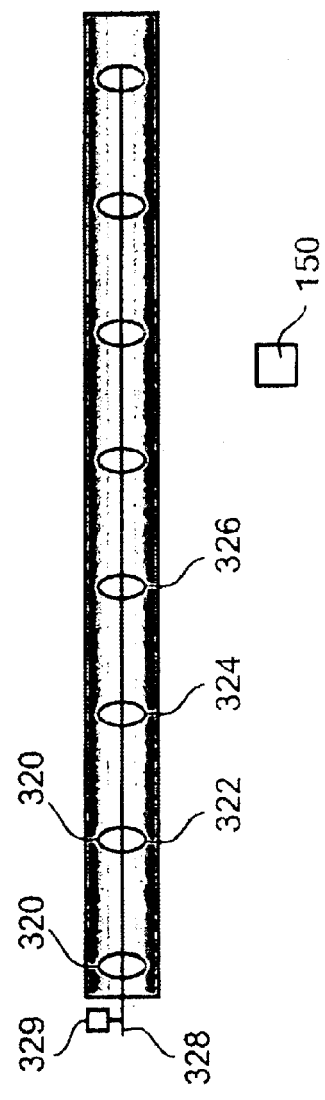
FIG. 17 presents an expanded view of a section of the catheter presented in FIG. 16, according to an embodiment of the present invention.

Attention is now drawn to FIG. 17, which presents an expanded view of a section of the catheter presented in FIG. 16, showing in greater detail a plurality of heat sensors placed along an external length of that catheter, according to an embodiment of the present invention. In an optional embodiment shown in FIG. 17, heat sensors 320 are shown to be linked by a data link 328, which may be a wire or bundle of wires operable to connect thermocouples 322 to an outside data receiver such as control module 150 described hereinabove. Data link 328 may also be a bundle of fiber-optic fibers 326, or any other sort of data communicator. Sensors may also be linked to an outside data collector such as control module 150 using a wireless communicator 329.

Figure 18:
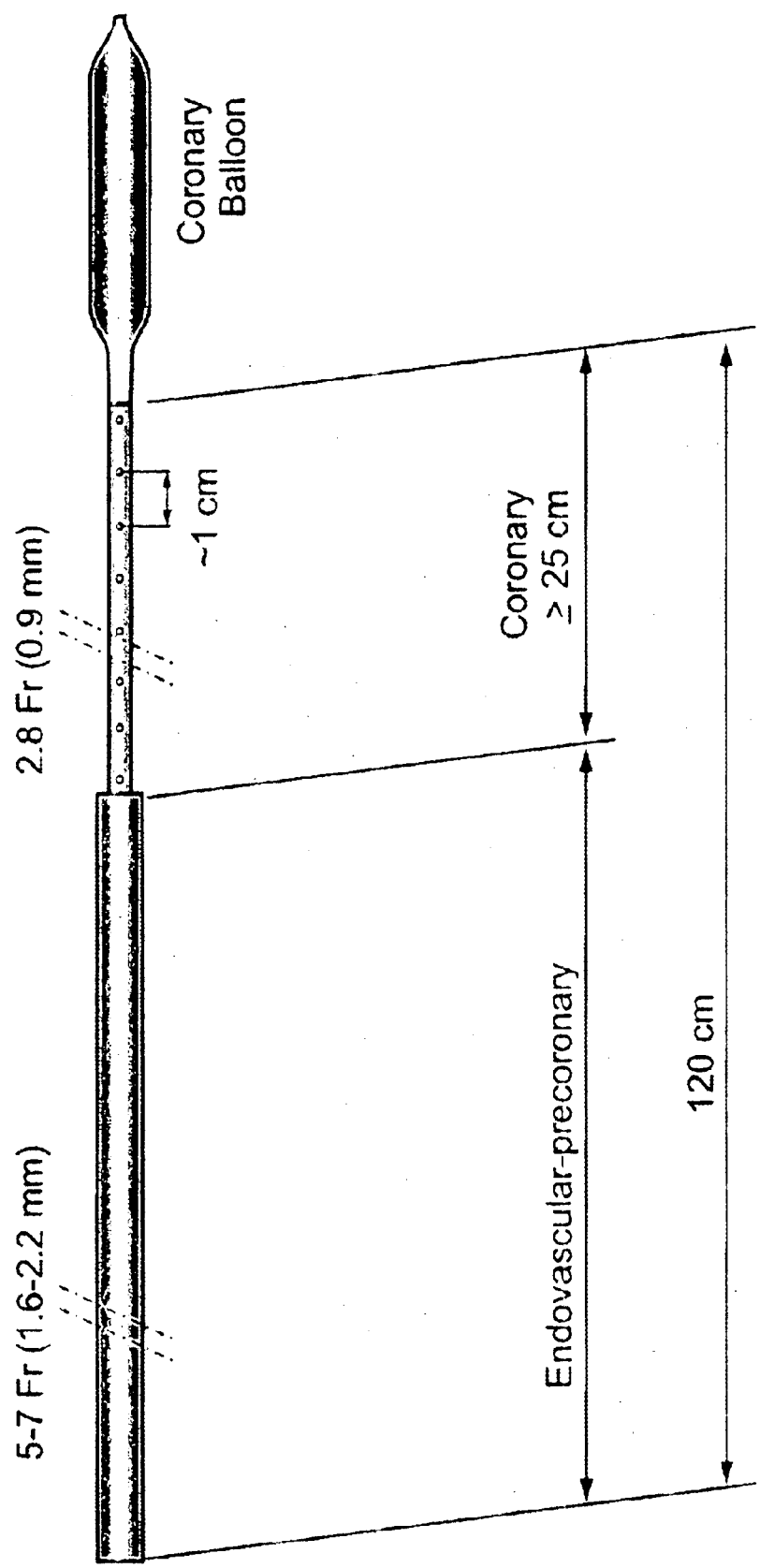
FIG. 18 presents recommended dimensions for various parts of an angioplasty balloon catheter comprising a plurality of external thermal sensors, according to a preferred embodiment of the present invention.

Attention is now drawn to FIG. 18, which presents recommended dimensions for various parts of an angioplasty balloon catheter comprising a plurality of external thermal sensors along a selected section thereof, according to a preferred embodiment of the present invention. The dimensions provided in FIG. 18 are presently recommended dimensions for a catheter combining the characteristics of catheter 100 and catheter 300, both defined and described hereinabove.

Figure 19:
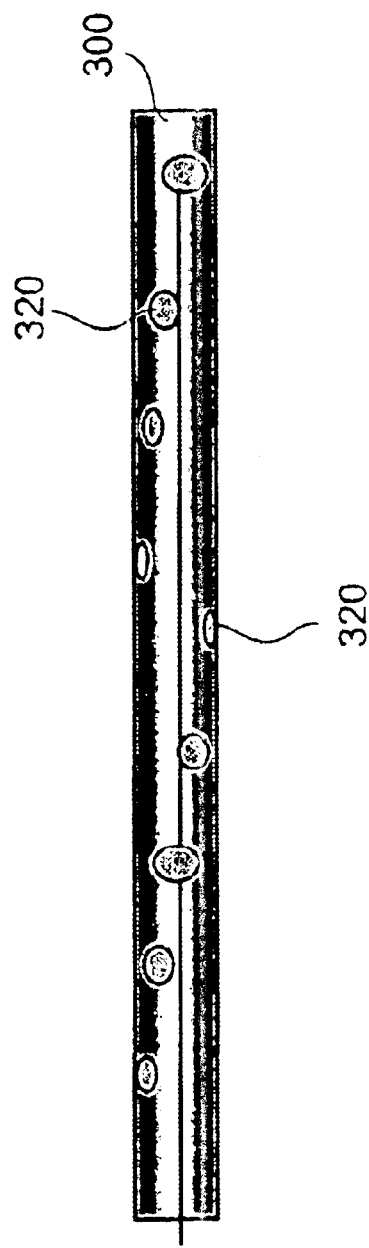
FIG. 19 a simplified schematic presenting an alternate scheme of placement for thermal sensors along a section of an angioplasty balloon catheter, according to an embodiment of the present invention.

Attention is now drawn to FIG. 19, which is a simplified schematic presenting an alternate scheme of placement for thermal sensors along a section of an angioplasty balloon catheter, according to an embodiment of the present invention. FIG. 19 presents a section of catheter similar to that presented in FIG. 17, with the difference that in an alternative construction presented in FIG. 19, thermal sensors 320 are spirally positioned around and along a selected segment of catheter 300, thus enabling temperature readings an all sides of catheter 300 along that selected length of catheter 300.

Figure 20:
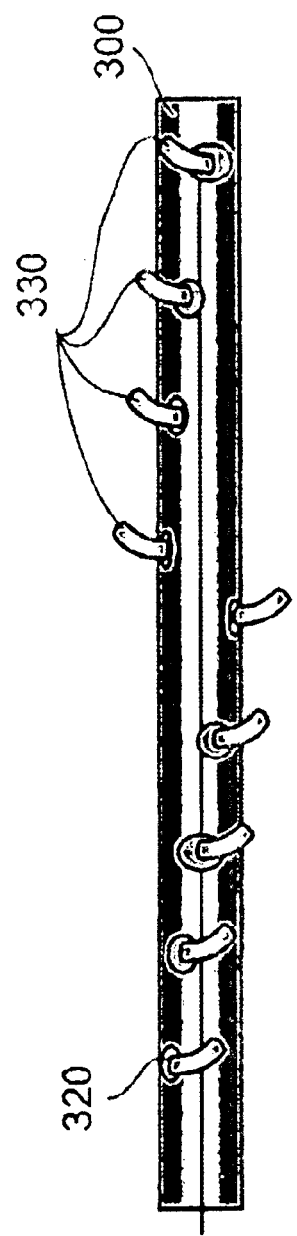
FIG. 20 is a simplified schematic presenting an alternate design for thermal sensors along a section of an angioplasty balloon catheter, according to an embodiment of the present invention.

Attention is now draw to FIG. 20, which is a simplified schematic presenting an alternate design for thermal sensors along a section of an angioplasty balloon catheter, according to an embodiment of the present invention. FIG. 20 presents a section of catheter similar to that presented in FIG. 19, with the difference that in an alternative construction presented in FIG. 20, thermal sensors 320 comprise a hair-like fiber 330 designed and constructed to facilitate transfer of heat between thermal sensors 320 and body tissues surrounding catheter 300 and adjacent to thermal sensors 320. Hair-like fibers 330 extend slightly outward from catheter 300, and thus are able to make physical contact with surrounding tissues, such as with portions of an arterial wall, when catheter 300 is inserted in an artery. Such contact enhances accuracy of temperature readings from sensors 320, in that such contact enhances ability of sensors 320 to report temperature of arterial wall tissues, as opposed, say, to temperature of blood flowing in an artery in which catheter 300 has been inserted.

Figure 21:
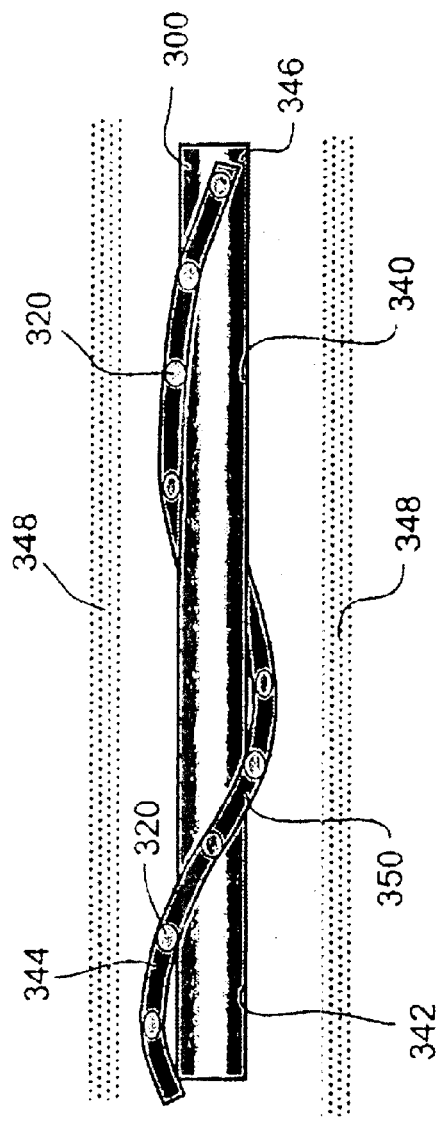
FIG. 21 is a simplified schematic presenting a further alternate design for thermal sensors along a section of an angioplasty balloon catheter, comprising an internal shaft and an external multi-sensor thermal sensing device, according to an embodiment of the present invention.

Attention is now drawn to FIG. 21, which is a simplified schematic presenting a further alternate design for thermal sensors along a section of an angioplasty balloon catheter, according to an embodiment of the present invention. FIG. 21 presents a section 340 of angioplasty balloon catheter 300, section 340 comprising an internal shaft 342 and an external multi-sensor thermal sensing device 350.

Shaft 342 is preferably a flexible tube. If catheter 300 is formed as catheter 100 described hereinabove, then shaft 342 will contain input gas lumen 104, exhaust gas lumen 130, and may contain various other optional features heretofore described.

Multi-sensor thermal sensing device 350 comprises a laterally contracting spring-like structure 344, preferably of spiral form, wrapped around shaft 342. Sensing device 350, preferably formed as a spiral sensing loop, further comprises a plurality of individually readable heat sensors 320, sensors 320 being substantially similar to heat sensors 320 previously described with reference to FIGS. 16, 17, 19, and 20.

Laterally contracting spring-like structure 344 is preferably anchored at its distal end to a fixed position 346 on shaft 342, whereas a proximal end of structure 344 is free to move longitudinally along shaft 342. In its relaxed position, laterally contracting spring-like structure 344 is designed and constructed to lie closely adjacent to shaft 342, as is shown in FIG. 21. Thus positioned, sensing device 350 does not add substantially to the diameter of catheter 300, and thus leaves catheter 300 free to move forward and backwards within an artery or other body conduit. With structure 344 positioned as depicted in FIG. 21, catheter 300, together with multi-sensor thermal sensing device 350, is free to move within arterial walls 348.

Figure 22:
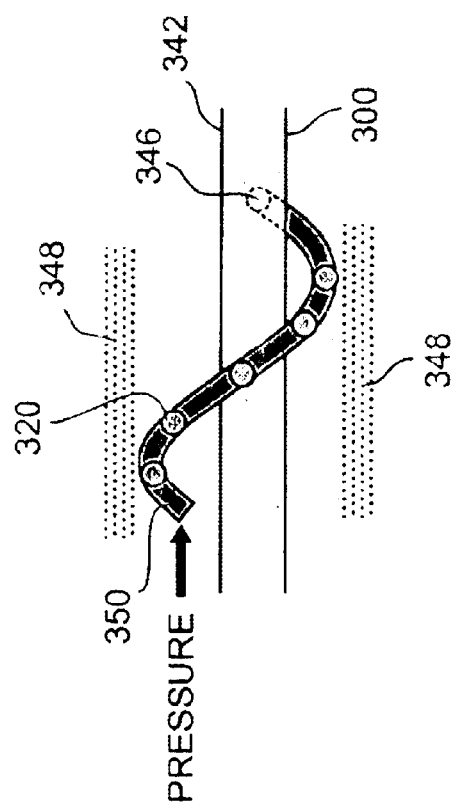
FIG. 22 is a simplified schematic of the apparatus of FIG. 21, shown in expanded position, according to an embodiment of the present invention.

Attention is now drawn to FIG. 22, which is a simplified schematic of the apparatus of FIG. 21, shown in expanded position. Structure 344 is so designed that when longitudinal pressure is applied to the proximal end of structure 344, towards fixed position 346, structure 344 is forced to expand, in spring-like manner, away from shaft 342. A movement of expansion thus engendered forces structure 344 into contact with arterial walls 348 surrounding catheter 300, as is shown in FIG. 22. Sensors 320 positioned along the length of structure 344 are thus forced into contact, or into close proximity, with body tissues lining arterial walls 348. Such contact or proximity enhances transfer of heat from those body tissues to sensors 320, thereby enhancing accuracy of thermal sensing by sensors 320.

Figure 23:
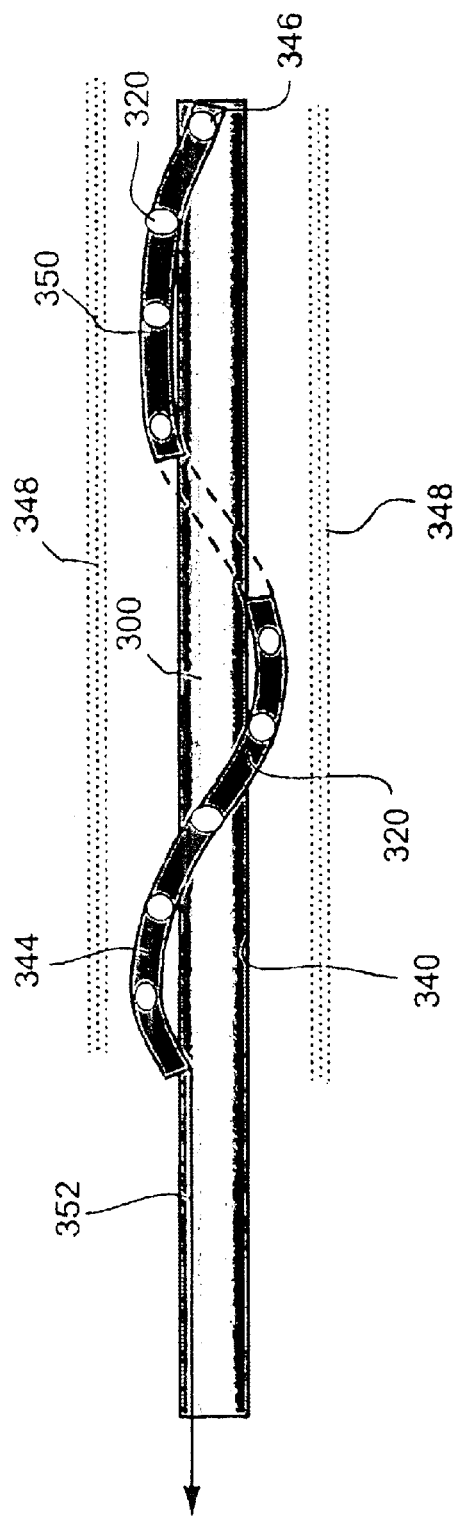
FIG. 23 is a simplified schematic of an alternative construction of a multi-sensor thermal sensing device, according to an embodiment of the present invention.
Figure 24:
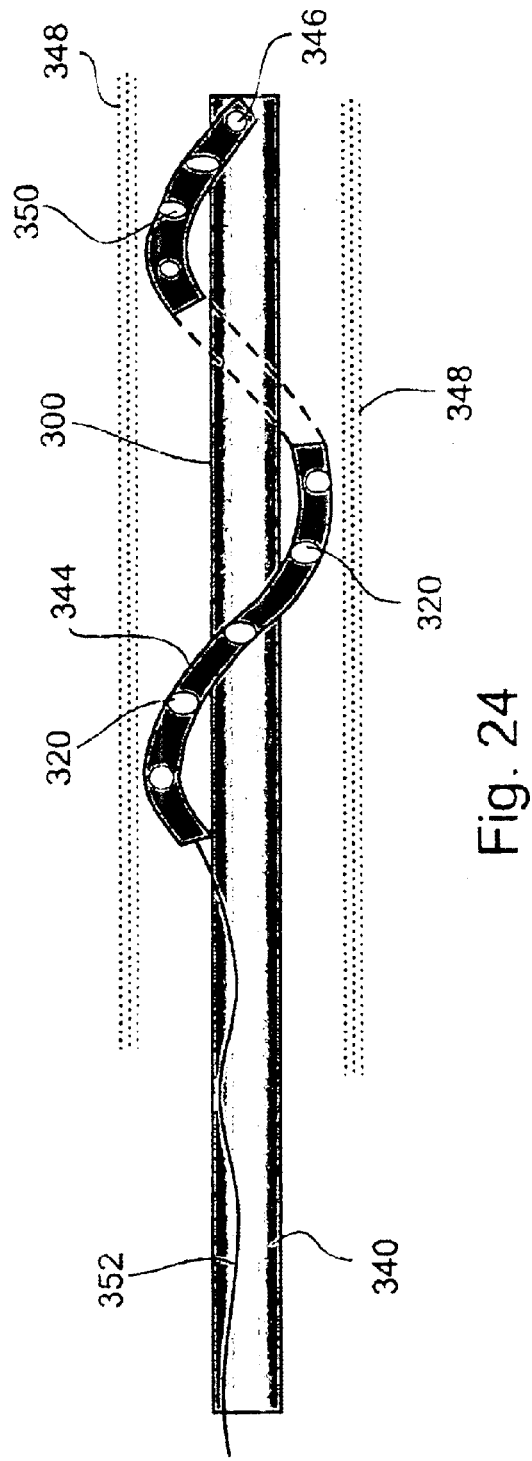
FIG. 24 shows the multi-sensor thermal sensing device of FIG. 23 in expanded position, according to an embodiment of the present invention.

Attention is now drawn to FIGS. 23 and 24, which show a slightly altered construction for multi-sensor thermal sensing device 350, according to a preferred embodiment of the present invention.

Design and construction of sensing device 350 as shown in FIGS. 23 and 24 is identical to that shown in FIGS. 21 and 22, with the exception that a spiral sensing loop formed as a laterally expanding spring-like structure 354 is substituted, in FIGS. 23 and 24, for a spiral sensing loop formed as laterally contracting spring-like structure 344 of FIGS. 21 and 22. Laterally expanding spring-like structure 354 is so constructed that in its relaxed state structure 354 tends to expand away from shaft 342, as shown in FIG. 24. A pulling attachment 352 is provided for pulling a proximal end of structure 354 away from a distal end of structure 354 anchored at position 346.

As shown in FIG. 23, during introduction of catheter 300 into an artery or other body conduit, pulling attachment 352 is pulled away from anchored position 346, thereby stretching structure 344 along shaft 342, thereby minimizing distance between device 350 and shaft 342, thereby facilitating movement of catheter 300 along an artery or other body cavity and minimizing friction or other interference between catheter 300 and arterial walls 348.

When catheter 300 is thought by an operator to be positioned in the vicinity of a lesion, pulling attachment 352 is released, allowing laterally expanding spring-like structure 354 to expand to its relaxed position, as shown in FIG. 24. As may be seen in the figure, structure 354 in its relaxed state tends to bring sensors 320 into close proximity to, or into contact with, body tissues surrounding catheter 300, such as arterial walls 348. Transfer of heat between arterial walls 348 and sensors 320 is thereby enhanced, thereby enabling device 350 to accurately sense and report temperatures at or near those body tissues.

Thus, to summarize FIGS. 21, 22, 23, and 24, each of the figures represents a catheter 300 having a plurality of thermal sensors distributed along an expandable spiral sensing loop having a distal end anchored to a distal portion of catheter 300. This expandable spiral sensing loop is spirally wound around a section of shaft of catheter 300, and is operable to expand away from that shaft, thereby enhancing thermal communication between sensors distributed along that sensing loop and body tissues adjacent to catheter 300. In the configuration presented by FIGS. 21 and 22, spiral sensing loop 344 is designed and constructed to expand away from said shaft of catheter 300 when a proximal end of that sensing loop is pushed toward an anchored distal end of that sensing loop. In the configuration presented by FIGS. 23 and 24, a spiral sensing loop is designed and constructed to contract toward a shaft of catheter 300 when a proximal end of that sensing loop is pulled away from an anchored distal end of that sensing loop.

Attention is now drawn to FIG. 25, which presents yet another alternative construction for a section of an angioplasty balloon catheter enabling multiple temperature measurements along a selected section of an artery, such temperature measurements being useable to assist in locating a site for angioplasty. In FIG. 25, a catheter 360 comprises a thermal sensor 320A attached to a moveable base 362, said moveable base being movably mounted on (and preferably mounted around) a shaft 342. A flexible yet semi-rigid push-pull connector 364 extends along a length of shaft 362, and may pass within a plurality of optional guides 366 which serve to maintain connector 364 adjacent to shaft 342. In use, an operator, either manually or utilizing a servomotor, causes 364 to push or pull base 362, causing base 362, and with it sensor 320, to slide along shaft 342. In use, heat sensor 320A is used to register temperature of tissues at a plurality of positions along a selected length of catheter 360, thus achieving a plurality of temperature measurements utilizing a single moveable heat sensor 320A (or alternatively, a small number of sensors 320) in place of a plurality of heat sensors 320 as was described above with reference to FIGS. 16–24. Thus, catheter 360 may be used in much the same way as catheter 300. In a preferred embodiment, sensor 320A is a fiber optic element moveable along catheter 360 and connectable to a thermographic camera 370 external to catheter 360.

Temperature-sensing apparatus described hereinabove with reference to FIGS. 16–17 and FIGS. 19–25 is particularly useful in positioning an angioplasty balloon catheter for an angioplasty procedure. A recommended procedure comprises a) introducing into an artery the angioplasty balloon catheter, the angioplasty balloon catheter having an inflatable balloon operable to perform angioplasty and a plurality of temperature sensors arranged along a selected section of the catheter, b) manipulating the catheter into a selected segment of the artery suspected of having an afflicted portion, c) operating the temperature sensors to determine temperatures at a plurality of sites along a selected segment of the artery, d) comparing the resultant temperature readings to determine a locus, within the inspected section of the artery, having temperatures high than those measured within other portions of the artery, and e) further manipulating the catheter so as to position the angioplasty balloon in a vicinity of that determined locus.

The procedure here described may be used to accurately positioning the angioplasty balloon of an angioplasty balloon catheter for an angioplasty procedure.

Similarly, use of temperature-sensing apparatus described hereinabove with reference to FIGS. 16–17 and FIGS. 19–24 enables a recommended method of treating a stenotic inflammation of an artery, the method comprising:

a) introducing into an artery an angioplasty balloon catheter such as catheter 300 described hereinabove, having an inflatable balloon 310 operable to perform angioplasty and a plurality of temperature sensors 320 arranged along a selected section of catheter 310, b) manipulating catheter 310 into a selected segment of an artery suspected of having an inflamed portion, c) operating temperature sensors 320 to determine temperatures at a plurality of sites along a selected segment of the artery, d) comparing temperature readings to determine a locus, within the selection section of the artery, having a temperatures high than those measured within other portions of the artery, e) further manipulating catheter 300 so as to position balloon 310 in a vicinity of the locus determined in step (d), and f) inflating balloon 310 so as to compress tissues around balloon 310 at the determined locus, thereby performing angioplasty, thereby treating said stenotic inflammation of said body conduit.

In a particularly recommended procedure, the above method of treating a stenotic inflammation of an artery comprises an additional step, namely utilizing a balloon catheter 300 equipped for cryogenic cooling of balloon 310 to cool balloon 310, and tissues surrounding balloon 310, during or immediately after angioplasty.

In a further recommended procedure, catheter 300 is implemented as catheter 100 described hereinabove, and cooling of inflated balloon 310 (also identifiable as balloon 110 described hereinabove) is accomplished using Joule-Thomson cooling of cooling gas introduced under pressure to a Joule-Thomson orifice (orifice 108) within balloon 310.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An angioplasty balloon catheter useable to treat arterial stenosis, comprising:

a) a gas input lumen for supplying a pressurized gas;

b) a first inflatable balloon containing a first variable volume;

c) a Joule-Thomson orifice for passing said pressurized gas from said gas input lumen into said first variable volume so as to cool and inflate said first inflatable balloon; and d) a plurality of thermal sensors operable to report external temperatures along a selected length of said catheter, thereby enabling said catheter to report a temperature gradient alone a selected segment of a body conduit when said catheter is inserted into said body conduit, said plurality of thermal sensors being distributed along an expandable spiral sensing loop having a distal end anchored to a distal portion of said catheter, said sensing loop being spirally wound around a section of shaft of said catheter and being operable to expand away from said shaft, thereby enhancing thermal communication between said sensors distributed along said sensing loop and body tissues adjacent to said catheter.

2. The catheter of claim 1, wherein said spiral sensing loop is designed and constructed to expand away from said shaft of said catheter when a proximal end of said sensing loop is pushed toward said anchored distal end of said sensing loop.

3. The catheter of claim 1, wherein said spiral sensing loop is designed and constructed to contract toward said shaft of said catheter when a proximal end of said sensing loop is pulled away from said anchored distal end of said sensing loop.

4. A system for angioplastic treatment of arterial stenosis and for reducing restenosis, comprising:

a) An angioplasty balloon catheter useable to treat arterial stenosis, having a gas input lumen for supplying a preasurized gas, a first inflatable balloon containing a first variable volume, and a Joule-Thomson orifice for passing said pressurized gas from said gas input lumen into said first variable volume of said first inflatable balloon so as to cool and inflate said first inflatable balloon;

b) a supply of compressed cooling gas operable to supply cooling gas to said gas input lumen;

c) a cooling gas input valve controlling delivery of compressed cooling gas from said supply of compressed cooling gas to said gas input lumen; and d) a plurality of thermal sensors operable to report external temperatures along a selected length of said catheter, thereby enabling said catheter to report a temperature gradient along a selected segment of a body conduit when said catheter is inserted into said body conduit, said plurality of thermal sensors being distributed along an expandable spiral sensing loop having a distal end anchored to a distal portion of said catheter, said sensing loop being spirally wound around a section of shaft of said catheter and being operable to expand away from said shaft, thereby enhancing thermal communication between said sensors distributed along said sensing loop and body tissues adjacent to said catheter.

5. The system of claim 4, wherein said spiral sensing loop is designed and constructed to expand away from said shaft of said catheter when a proximal end of said sensing loop is pushed toward said anchored distal end of said sensing loop.

6. The system of claim 4, wherein said spiral sensing loop is designed and constructed to contact toward said shaft of said catheter when a proximal end of said sensing loop is pulled away from said anchored distal end of said sensing loop.

* * * * *